US010328023B2

(12) United States Patent
Romanoschi et al.

(10) Patent No.: US 10,328,023 B2
(45) Date of Patent: Jun. 25, 2019

(54) MULTICOMPONENT GUMMY COMPOSITIONS WITH HARD CORE

(71) Applicant: Church & Dwight, Co., Inc., Princeton, NJ (US)

(72) Inventors: Ovidiu Romanoschi, Highland Park, NJ (US); Caryn Oryniak, Hillsborough, NJ (US); Luis C. Muniz, Brooklyn, NY (US); Hiep Huatan, Kent (GB); Nazim Kanji, Leicester (GB); Huw Jones, Nottingham (GB); Lindsey Bagley, Berkshire (GB); Graham Godfrey, Worcestershire (GB)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 15/092,283

(22) Filed: Apr. 6, 2016

(65) Prior Publication Data

US 2016/0296474 A1    Oct. 13, 2016

Related U.S. Application Data

(60) Provisional application No. 62/144,224, filed on Apr. 7, 2015, provisional application No. 62/238,947, filed on Oct. 8, 2015.

(51) Int. Cl.
*A61K 9/00* (2006.01)
*A61K 45/06* (2006.01)
(Continued)

(52) U.S. Cl.
CPC .............. *A61K 9/0056* (2013.01); *A23G 3/36* (2013.01); *A23G 3/54* (2013.01); *A61K 9/2009* (2013.01);
(Continued)

(58) Field of Classification Search
CPC .... A61K 9/209; A61K 31/375; A61K 9/0056; A61K 9/2095; A61K 9/2009;
(Continued)

(56) References Cited

U.S. PATENT DOCUMENTS

| 5,004,595 A | 4/1991 | Cherukuri et al. |
| 5,690,990 A | 11/1997 | Bonner et al. |

(Continued)

FOREIGN PATENT DOCUMENTS

| EP | 1136067 A1 | 9/2001 |
| WO | 00/61116 A2 | 10/2000 |

(Continued)

OTHER PUBLICATIONS

Iwamoto, et al., "Preparation of Gelatin Microbeads With a Narrow Size Distribution Using Microchannel Emulsification", AAPS PharmSciTech 2002; 3 (3) article 25 (http://www.aapspharmscitech.org).; published Aug. 8, 2002, pp. 1-5.

(Continued)

*Primary Examiner* — Blessing M Fubara
(74) *Attorney, Agent, or Firm* — Church & Dwight Co., Inc.

(57) ABSTRACT

The present disclosure provides oral, chewable dosage forms that are suitable for delivery of one or more active ingredients to a consumer, particularly a human individual. The dosage forms can be configured as multicomponent compositions formed of: a first component including a gummy composition; a second component that is a particulate material or is a pre-formed solid unit or plurality of pre-formed solid units; and an active ingredient. The second component can be, for example, in the form of a pharmaceutically acceptable oral dosage unit, such as a tablet, a caplet, a soft shell capsule, a hard shell capsule, a microcapsule, or a pastille.

22 Claims, 4 Drawing Sheets

(51) Int. Cl.

| | | |
|---|---|---|
| A23G 3/54 | (2006.01) | |
| A23G 3/36 | (2006.01) | |
| A61K 9/24 | (2006.01) | |
| A61K 9/20 | (2006.01) | |
| A61K 31/375 | (2006.01) | |
| A61K 31/19 | (2006.01) | |
| A61K 31/519 | (2006.01) | |
| A61K 31/167 | (2006.01) | |
| A61K 31/197 | (2006.01) | |
| A61K 31/616 | (2006.01) | |
| A61K 31/4545 | (2006.01) | |
| A61K 33/42 | (2006.01) | |

(52) U.S. Cl.
CPC .......... *A61K 9/2013* (2013.01); *A61K 9/2018* (2013.01); *A61K 9/2027* (2013.01); *A61K 9/2054* (2013.01); *A61K 9/2072* (2013.01); *A61K 31/167* (2013.01); *A61K 31/19* (2013.01); *A61K 31/197* (2013.01); *A61K 31/375* (2013.01); *A61K 31/4545* (2013.01); *A61K 31/519* (2013.01); *A61K 31/616* (2013.01); *A61K 33/42* (2013.01); *A61K 45/06* (2013.01); *A23V 2002/00* (2013.01)

(58) Field of Classification Search
CPC .. A61K 9/2013; A61K 9/2018; A61K 9/2072; A61K 9/2054; A61K 9/2027; A61K 31/519; A61K 31/4545; A61K 31/616; A61K 31/197; A61K 31/19; A61K 31/167; A61K 33/42; A23G 3/36; A23G 3/54

See application file for complete search history.

(56) References Cited

U.S. PATENT DOCUMENTS

| | | |
|---|---|---|
| 5,759,599 A | 6/1998 | Wampler et al. |
| 6,039,901 A | 3/2000 | Soper et al. |
| 6,045,835 A | 4/2000 | Soper et al. |
| 6,056,992 A | 5/2000 | Lew et al. |
| 6,060,078 A | 5/2000 | Lee |
| 6,106,875 A | 8/2000 | Soper et al. |
| 6,117,455 A | 9/2000 | Takada et al. |
| 6,482,433 B1 | 11/2002 | Deroos et al. |
| 6,929,814 B2 | 8/2005 | Bouwmeesters et al. |
| 8,404,275 B2 | 3/2013 | Habboushe |
| 8,414,917 B2 | 4/2013 | Asano et al. |
| 8,673,190 B2 | 3/2014 | Sowden et al. |
| 2003/0086960 A1 | 5/2003 | Seielstad et al. |
| 2003/0219514 A1 | 11/2003 | Jones et al. |
| 2005/0260329 A1 | 11/2005 | Yusuf et al. |
| 2006/0263475 A1* | 11/2006 | Jani ........................ A23G 4/064 426/3 |
| 2007/0141198 A1 | 6/2007 | Yang |
| 2008/0063748 A1 | 3/2008 | Massey et al. |
| 2008/0248079 A1 | 10/2008 | Dempsey et al. |
| 2008/0248089 A1 | 10/2008 | Bugge et al. |
| 2010/0003390 A1 | 1/2010 | Rifkin et al. |
| 2010/0034894 A1* | 2/2010 | Szymczak ........... A61K 9/1623 424/490 |
| 2010/0166810 A1 | 7/2010 | Habboushe |
| 2010/0166914 A1 | 7/2010 | Herron et al. |
| 2010/0226904 A1 | 9/2010 | Davis |
| 2010/0330558 A1 | 12/2010 | Davis |
| 2012/0035277 A1 | 2/2012 | Davis |
| 2013/0189361 A1* | 7/2013 | Habboushe .......... A61K 9/0056 424/468 |
| 2013/0209540 A1 | 8/2013 | Duggins et al. |
| 2013/0287899 A1 | 10/2013 | Rifkin |
| 2013/0316053 A1 | 11/2013 | Rifkin |
| 2014/0271853 A1* | 9/2014 | Hall .................... A61K 9/0056 424/472 |
| 2016/0045433 A1 | 2/2016 | Whitney |

FOREIGN PATENT DOCUMENTS

| | | |
|---|---|---|
| WO | 2009007769 A1 | 1/2009 |
| WO | 2012106582 | 8/2012 |
| WO | 2012126770 A1 | 9/2012 |
| WO | 2013136183 A2 | 9/2013 |

OTHER PUBLICATIONS

Singh, et al., "Microencapsulation: A promising technique for controlled drug delivery", Res Pharm Sci. Jul.-Dec. 2010; 5(2): published Jun. 1, 2010, pp. 65-77.

International Search Report and Written Opinion for PCT Application No. PCT/US16/26228, dated Jul. 1, 2016, pp. 1-10.

International Search Report and Written Opinion for PCT Application No. PCT/US16/26219, dated Jul. 12, 2016, pp. 1-11.

* cited by examiner

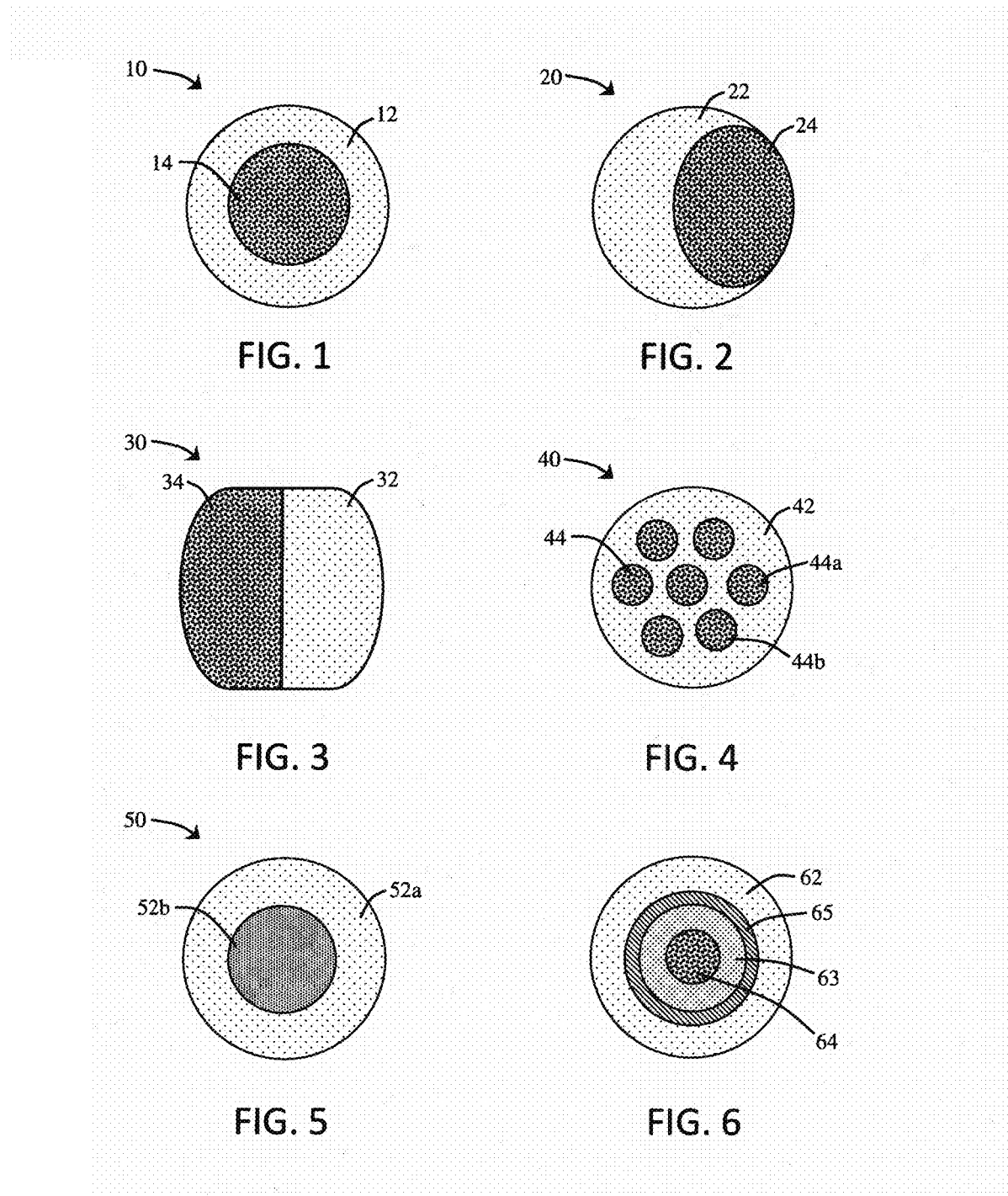

MULTICOMPONENT GUMMY COMPOSITIONS WITH HARD CORE

FIELD OF THE DISCLOSURE

The present disclosure relates to orally ingestible dosage forms. The dosage forms can comprise at least two different compositions include a multicomponent unit in a variety of combinations.

BACKGROUND

Oral dosing of many materials with desirable properties and functions can be problematic when provided in a chewable form because the intrinsic taste of such materials can be unpleasant, particularly to children. The intrinsic bitterness of certain active pharmaceutical ingredients (APIs) in particular can present a major obstacle to the acceptance, compliance, and effectiveness of treatments including oral, chewable dosing.

Previous approaches to addressing the problem of poor palatability of certain materials have been based mainly on nullifying undesirable tastes using flavor additives, chemical chelation (e.g., using ion exchange resins and β-cyclodextrins) and physical encapsulation. These systems can be adapted into solid dosage forms or liquid based formulations as solutions, suspensions, or multi-phase emulsions.

Generally, most children cannot swallow traditional solid dosage forms (e.g., tablets and capsules) at least until the age of six due to the risk of choking. For young children (i.e., <2 years of age), liquid dosage forms are preferred as dosing can be facilitated via an oral syringe or spoon. These dosage forms, however, can be problematic as they accentuate the taste issue of bitter active ingredients in solution. Suspensions can improve taste-masking effectiveness, however, mouth feel and grittiness is often the overriding issue.

Alternative non-liquid formulations have been designed to compensate for the poor dosing acceptability and taste limitation of liquid-based formulations for older children (>2 years of age). These formulations typically can include chewable tablets, gummies, specially compounded lollipops, and other confectionary mimics.

Gummy dosage forms are particularly effective for enabling compliant dosing in children as they provide a palatable, chewable base and can incorporate active ingredient(s) that are generally of very low dose, have the ability to withstand the high thermal stress of the gummy manufacturing process, and have low intrinsic taste response. Moreover, while gummy dosage forms provide the basis for effective dosing of active ingredients to children, their application for the delivery of APIs and like materials has been highly restrictive due to the limited number of active ingredients that are compatible with the gummy dosage-platform.

Gummy dosage forms have previously been produced by compounding a variety of ingredients (e.g., sugars, corn syrup, water, gelatin, flavors, and other sweeteners) then cooking the mixture at high temperatures (e.g., up to about 240° C.) before depositing the cooked mixture into preformed molds. The incorporation of the active ingredients can be facilitated only during the initial compounding step prior to cooking. The viscosity of the cooked mixture is generally too high to enable the active ingredients to be added retrospectively. As a result of the very high thermal stress of the cooking process, the active ingredients can be subject to significant chemical and/or physical degradation during the manufacture of gummies. Accordingly, the practice of utilizing overages (including excess active ingredient to off-set the losses due to degradation during manufacturing) has been instituted.

The use of overages to off-set gross manufacturing losses in gummy dosage forms is permitted only for some functional actives that do not present safety concerns. The application of this practice for APIs is not generally feasible as it may lead to significant efficacy, safety, and regulatory issues. In addition, as the quality control requirements for APIs (i.e., claimed dose of active, content uniformity, degradation limits, etc.) are generally much more stringent than food-based functional additives, the suitability of gummies as an oral delivery platform becomes even more prohibitive. As such, there remains a need in the art for oral, chewable dosage forms suitable for delivery of APIs and the like in a manner where active ingredient content can be closely controlled throughout manufacturing to provide a resulting dosage form of consistent quality and desirable palatability.

SUMMARY OF THE DISCLOSURE

The present disclosure provides chewable, multicomponent dosage forms that are adapted for the delivery of a wide variety of active ingredients to individuals that may have difficulty in swallowing conventional oral dosage forms (e.g., children and geriatric adults) and/or those who have an aversion to the taste of the active ingredients or have dosing fatigue to swallowable pills. The present disclosure provides for formulations of active ingredients in dosage forms that are stable during storage under ambient conditions and have improved palatability attributes over conventional oral dosage forms, such as conventional tablets and capsules.

In one or more embodiments, a multicomponent composition according to the present disclosure can be configured for oral administration, and can particularly provide improved palatability for an active ingredient that can be included in the composition. For example, the multicomponent composition can comprise: a first component that is a gummy composition; a second component that is in the form of a particulate material or is a pre-formed solid unit or plurality of pre-formed units; and an active ingredient. In some embodiments, the first component can comprise at least a portion of an outer surface of the multicomponent composition. In further embodiments, the second component can comprise at least a portion of the outer surface of the multicomponent composition.

A multicomponent composition according to the present disclosure can be further defined in relation to one or more of the following statements, which statements can be combined in any number and order.

The first component can completely surround the second component such that the first component is substantially a shell surrounding at least one core formed of the second component.

The multicomponent composition can further comprise a third component configured as a layer between the first component and the second component.

The third component can be configured as a barrier layer that substantially prevents passage of water between the first component and the second component.

The second component can comprise a plurality of units.

The active ingredient can be included in the second component.

The active ingredient can be included in the first component.

The active ingredient can be a natural or synthetic substance that is recognized as being beneficial to human health.

The active ingredient can be selected from the group consisting of non-steroidal anti-inflammatory drugs (NSAIDs), analgesics, antihistamines, decongestants, expectorants, antitussives, sleep aids, antibiotics, laxatives, anti-diarrheals, anthelmintics, antacids, vitamins, minerals, phytonutrients, fiber, fatty acids, amino acids, polypeptides, botanicals, herbs, prebiotics, probiotics, and combinations thereof.

The gummy composition can be elastic or viscoelastic.

The gummy composition can comprise about 70% to about 94% w/w of one or more hydrophilic bulking agents, about 1% to about 20% w/w of the one or more hydrophilic, long-chain polymers, and about 5% to about 35% w/w of a water source.

The one or more bulking agents can comprise one or more saccharides or saccharide derivatives.

The one or more bulking agents can comprise one or more hydrogenated carbohydrates.

The one or more hydrophilic bulking agents can include one or both of sugar solids and granulated sugar.

The one or more hydrophilic bulking agents can include glucose, sucrose, and sorbitol.

The active ingredient can be in an encapsulated form.

The composition in the form of a compressed solid can comprise one or more ingredients selected from the group consisting of saccharides, saccharide derivatives, lipids, cellulosic polymers, cellulosic polymer derivatives, inorganic salts, and combinations thereof.

The second composition is a pre-formed solid unit or plurality of units in the form of one or more of a tablet, a caplet, a hard shell capsule, a soft shell capsule, a microcapsule, and a pastille.

The second composition is a pre-formed tablet having a hardness of about 2 Kp to about 35 Kp.

The pre-formed tablet can be orally disintegrable or dissolvable.

The pre-formed tablet can have a hardness of about 4 Kp to about 20 Kp.

The pre-formed tablet can comprise about 5% to about 80% w/w of one or more bulking agents, about 0.1% to about 15% w/w of one or more disintegrants, about 0.05% to about 5% w/w of one or more processing aids, and the active ingredient in an amount of about 0.1% to about 60% w/w.

The pre-formed tablet can be stable such that the active ingredient exhibits substantially no degradation when the core composition is stored for a time of 20 days at a temperature of 40° C. and a relative humidity of 75%.

The pre-formed tablet can be stable such that, separate from the first component, the pre-formed tablet absorbs less than about 5% by weight of water (based on the weight of the tabletted composition) over a time of 14 days at a temperature of 40° C. and a relative humidity of 75%.

The pre-formed tablet can have a maximum dimension of about 6 mm to about 12 mm.

The pre-formed tablet can have a diameter of about 6 mm to about 12 mm and a thickness of about 0.5 mm to 8 mm.

The pre-formed tablet can have a maximum dimension of about 2 mm to about 10 mm.

The pre-formed tablet can have a diameter of about 2 mm to about 10 mm and a thickness of about 0.5 mm to 6 mm.

The pre-formed tablet, prior to combination with the first component, can be friable and have a brittleness index of about 0.5 to about 0.95.

The second composition is a pre-formed unit of a chewy composition having a hardness of about 4 Kp to about 20 Kp.

The pre-formed unit of the chewy composition can comprise about 10% to about 60% w/w of one or more bulking agents, about 5% to about 60% w/w of one or more hydrophilic polymers, about 0.05% to 5% of one or more processing aids, optionally one or more disintegrants, and the active agent in an amount of about 0.1% to about 60% w/w.

The pre-formed unit of the chewy composition can be water stable such that, separate from the first component, the pre-formed unit of the chewy composition absorbs less than about 10% by weight of water (based on the weight of the chewy composition) over a time of 5 days at a temperature of 40° C. and a relative humidity of 75%.

The pre-formed unit of the chewy composition can be stable such that the active ingredient exhibits substantially no degradation when the chewy composition is stored for a time of 11 days at a temperature of 40° C. and a relative humidity of 75%.

The pre-formed unit of the chewy composition can have a maximum dimension of about 6 mm to about 12 mm.

The pre-formed unit of the chewy composition can have a diameter of about 6 mm to about 12 mm and a thickness of about 0.5 mm to 8 mm.

The second composition can be a pre-formed unit of a lipidic composition that can comprise one or more lipidic materials and one or more bulking agents.

The one or more lipidic materials can be selected from the group consisting of vegetable fats, nut fats, seed fats, and combinations thereof.

The one or more lipidic materials can comprise cocoa fat.

The pre-formed unit of the lipidic composition can comprise about 10% to about 60% w/w of the one or more lipid materials and about 10% to about 60% w/w of the one or more bulking agents.

The active ingredient can be present in the pre-formed unit of the lipidic composition.

The pre-formed unit of the lipidic composition can be stable such that, after being stored for a time of 28 days at a temperature of 50° C. and a relative humidity of 60%, the pre-formed unit of the lipidic composition comprises less than about 2% by weight of active ingredient degradation products relative to the weight of the active ingredient.

The pre-formed unit of the lipidic composition can have a diameter of about 0.5 mm to about 10 mm.

The multicomponent composition can include an outer layer surrounding the first component and the second component.

The second composition can be a particulate material. The particulate material specifically can be in the form of a powder, granules, beads, or the like.

BRIEF DESCRIPTION OF THE FIGURES

FIG. 1 is a cross-section of a multicomponent composition according to an exemplary embodiment of the present disclosure illustrating a gummy composition completely surrounding a second composition in a shell/core configuration;

FIG. 2 is a cross-section of a multicomponent composition according to an exemplary embodiment of the present disclosure illustrating a gummy composition partially surrounding a second composition;

FIG. 3 is a cross-section of a multicomponent composition according to an exemplary embodiment of the present disclosure illustrating a gummy composition and a second composition substantially in a side-by-side configuration;

FIG. 4 is a cross-section of a multicomponent composition according to an exemplary embodiment of the present disclosure illustrating a plurality of second compositions configured interior to a gummy composition;

FIG. 5 is a cross-section of a multicomponent composition according to an exemplary embodiment of the present disclosure illustrating a first gummy composition surrounding a second gummy composition;

FIG. 6 is a cross-section of a multicomponent composition according to an exemplary embodiment of the present disclosure illustrating an outer gummy composition and an inner composition with a first intervening layer and a second intervening layer;

DETAILED DESCRIPTION OF THE DISCLOSURE

Figure 7:
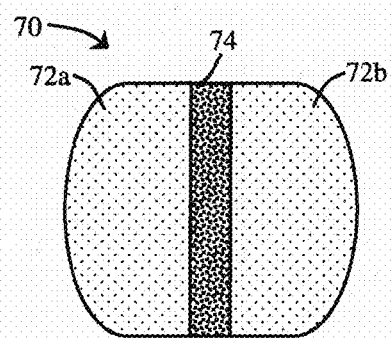
FIG. 7 is a cross-section of a multicomponent composition according to an exemplary embodiment of the present disclosure illustrating a second composition between two gummy compositions

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to oral, multicomponent dosage forms that are suitable for delivery of active ingredients in a manner that is highly palatable and that thusly improves compliance with dosing requirements for the active ingredients. In one or more embodiments, the dosage forms can comprise a gummy composition as at least one of the components. The gummy composition may completely or at least partially surround one or more different compositions that are also included in the multicomponent dosage form. While two or more different gummy compositions may be used, in some embodiments, multicomponent dosage forms of the present disclosure can comprise at least one gummy composition and at least one different composition that is also in a different form. Such different composition can be referred to as a second composition (the gummy composition being a first composition). The multicomponent compositions thus may comprise at least two, at least three, at least four, or even more different compositions. The active ingredient can be included in the gummy composition, in the one or more different composition, or in the gummy composition and one or more of the different composition(s).

A "gummy" as used herein is understood to refer to a confectionary that can be defined by its compositional nature, as otherwise described herein, and also by its chewy texture and mouthfeel. Gummy bears, gummy worms, and other gummy candies are known in the art, and a person of ordinary skill in the art would understand the term "gummy" to refer to a composition having such texture and mouthfeel.

An "active ingredient" as used herein can include any compound, composition, or like material that may be included in a dosage form for delivery to an individual to achieve any one or more of a desired nutritional purpose, medicinal purpose, and therapeutic purpose. In some embodiments, an active ingredient can be an API. Non-limiting examples of APIs include non-steroidal anti-inflammatory drugs (NSAIDs—e.g., ibuprofen, diclofenac, and naproxen), analgesics (e.g., acetaminophen, aspirin), antihistamines, decongestants, antitussives, expectorants, sleep aids, antibiotics, laxatives, anti-diarrheals, anthelmintics, and antacids. Further, non-limiting examples of materials that may be included as an active ingredient include vitamins, minerals, phytonutrients (e.g., carotenoids, flavonoids, resveratrol, and glucosinolates), fiber, fatty acids, amino acids, polypeptides, and botanicals. An active ingredient can include any plant-derived material that is safe for human consumption, including herbal extracts, botanical extracts, and the like. Other materials, such as prebiotics, probiotics, can also be used as an active ingredient. In some embodiments, an active agent according to the present disclosure may be classified as dietary supplement according to the Dietary Supplement Health and Education Act of 1994, whereby a dietary supplement is defined to mean a product (other than tobacco) intended to supplement the diet that bears or contains one or more of the following dietary ingredients: a vitamin, a mineral, an herb or other botanical, an amino acid, a dietary substance for use by man to supplement the diet by increasing the total dietary intake; or a concentrate, metabolite, constituent, extract, or combination of any of the aforementioned ingredients.

The multicomponent dosage forms can be configured with the different compositions combined in a variety of conformations. In some embodiments, the gummy composition may partially or completely surround the second composition. For example, FIG. 1 illustrates a multicomponent composition 10 wherein a gummy composition 12 completely surrounds a second composition 14, thus forming a shell/core configuration. FIG. 2 illustrates, as a further example, a multicomponent composition 20 wherein a gummy composition 22 partially surrounds a second composition 24, and FIG. 3, for example, illustrates a multicomponent composition 30 wherein a gummy composition 32 and a second composition 34 are substantially in a side-by-side configuration. As a further example, FIG. 4 illustrates a multicomponent composition 40 wherein a plurality of second compositions 44 are configured interior to a gummy composition 42. The plurality of second compositions 44 may be separate units formed of the same composition or may be separate units formed from two or more different compositions (e.g., units 44a and 44b being formed of different compositions). The second compositions 44 illustrated in FIG. 4 may be, for example, minitabs as further described herein. In the illustrated embodiments, it is understood that one or more active agents may be included in the gummy composition, the second composition, or both. In a further example shown in FIG. 5, a first gummy composition 52*a* can surround a second gummy composition 52*b*. In such embodiments, one or more active agents may be included in one or both of the compositions. As before, the first gummy composition can completely or partially surround the second gummy composition, or the gummy compositions may be in a side-by-side arrangement. In some embodiments, the multicomponent dosage form can comprise a plurality of layers. As illustrated in FIG. 6, the multicomponent composition 60 can comprise an outer gummy composition 62 and an inner composition 64 with a first intervening layer 63 and a second intervening layer 65. The layers can have different compositions and can be of different thicknesses. Active agents may be provided in any or all of the gummy composition, the inner composition. 64, the first intervening layer 63, and the second intervening layer 65. It is understood that the nature of such dosage forms is not limited by the naming, and each of elements 62, 63, 64, and 65 may be considered layers. In some embodiments, a stacked configuration may be utilized. For example, as seen in FIG. 7, the multicomponent composition 70 can comprise a second composition 74 between two gummy compositions 72*a* and 72*b*. It is understood that the reverse situation is also encompassed wherein a gummy composition may be provided between two different compositions (i.e., between two layers of the second composition or between a layer of the second composition and a layer of a third composition).

In one or more embodiments, a dosage form as described herein can be adapted to compartmentalize the active ingredient into a portion of the overall dosage form that is separate from the gummy composition. A compartmentalized gummy dosage form can afford stability for the active ingredient(s) and can permit consistent release of the actives from the gummy dosage form while also providing optimal organoleptic response to aid user acceptance and compliance. Compartmentalization is further beneficial for any one or more of the following: the active ingredients are not subject to the same thermal stress that is imparted on the gummy base during the cooking and depositing process; the active ingredients are physically separated from the gummy base to limit the potential for chemical and physical interactions during the manufacture and following long-term storage; the active ingredients can be controlled to a high quality limit in respect of dose, dose uniformity, and degradation limit compared to the gummy base; and the active ingredients are subject to no overage inclusion or only limited overage inclusion to take account of gross losses during manufacture. While it is thus evident that compartmentalization can be beneficial, in one or more embodiments, active ingredients can be included in a gummy composition, particularly if the above considerations are not critical to the overall nature of the dosage form. Likewise, active ingredients may be present in both the gummy composition as well as one or more further compositions included in the multicomponent dosage form.

Where compartmentalization is desirable, the multicomponent dosage forms of the present disclosure can be particularly useful. For example, a compartmentalized gummy dosage form can be configured such that the active ingredient is partially or completely present within a second composition that is provided in combination with the gummy composition. As already noted above, the second composition may be in the form of one or more solid or semi-solid cores that are embedded within the gummy composition so as to be partially or completely surrounded by the gummy composition, the second composition may be in the form of a layer present within the multicomponent dosage form, and/or the second composition may be substantially attached, adhered, or otherwise interconnected with the gummy composition (e.g., the side-by-side arrangement). Separating the active ingredient from the gummy base via compartmentalization in the second composition allows the active ingredient (within the second composition) to be incorporated into the gummy dosage form during a downstream processing step and not the upstream cooking step, which carries the highest thermal stress. In addition, by separating the compounding step for the second composition from the manufacturing process for the gummy composition (particularly one or more deposition steps), the control of the key quality attributes for the active ingredient is not limited by the inflexible and stress-bound process for forming the gummy composition.

Figure 8:
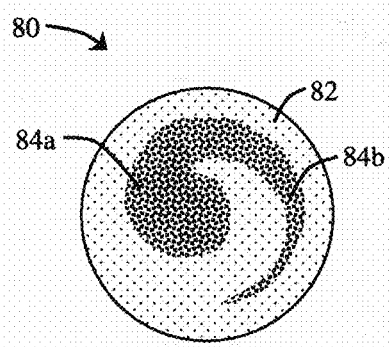
FIG. 8 is a cross-section of a multicomponent composition according to an exemplary embodiment of the present disclosure illustrating a gummy composition and a second composition that is partially blended into the gummy composition.

Although compartmentalization can be advantageous, it is not required. In some embodiments, the different compositions forming the multicomponent dosage forms can be partially blended or otherwise combined so that the second composition is not necessarily in the form of a discrete "unit" within the gummy composition. As a non-limiting example, as seen in FIG. 8, the multicomponent composition 80 can comprise a gummy composition 82 and a second composition 84 that is partially blended into the gummy composition. As illustrated, the second composition 84 has a main body 84*a* and a tail 84*b* that substantially blends into the gummy composition. Such conformation may be referred to as a "swirl", and other like structures are also encompassed by the present disclosure.

The nature of the second composition can be particularly relevant in providing the significant advantages over conventional gummy matrix formulations. In particular, the second composition can be provided with specific properties that confer consistent release of the active ingredient and maximize the organoleptic response of the overall gummy dosage form.

In the multicomponent dosage forms of the present disclosure, the gummy composition, in some embodiments, can be configured according to known recipes. For example, it is generally known to prepare a gummy composition by combining gellants, sweeteners, water, colors, and flavors. The combined materials can be heated to form a thickened slurry, which can then be poured into molds to provide the desired shape. The molds may be coated with a release agent or formed from a material designed to facilitate release. The formed gummy compositions are allowed to cool and set to the final, desired shape when released from the molds. If desired, one or more coating layers can be applied to the formed gummy composition.

In one or more embodiments, a gummy composition utilized according to the present disclosure can be a hydrocolloid system. In particular, a hydrocolloid system can comprise one or more hydrophilic long-chain polymers, one or more hydrophilic bulking agents, and a water source. Optionally, the hydrocolloid system can include one or more further ingredients, such as pH modifiers, coloring agents, and/or flavoring agents. The outer composition particularly can be substantially a gummy base. The outer composition may particularly be characterized as being an elastic or viscoelastic material.

Hydrophilic, long-chain polymers useful in a hydrocolloid system according to the present disclosure include long chain carbohydrates (e.g., polysaccharides) as well as various proteins. The hydrophilic, long-chain polymer preferably is configured to thicken and form a gel upon hydration (with or without heating). Non-limiting examples of hydrophilic, long-chain polymers that may be included in a hydrocolloid system for use as a gummy composition according to the present disclosure include: gelatin, pectin, carrageenan, gellan gum, locust bean gum, gum arabic, xanthan gum, starch, methylcellulose, agar, konjac, alginates, and combinations thereof (including single, binary, tertiary, or quaternary blends).

Hydrophilic bulking agent useful in a hydrocolloid system according to the present disclosure include saccharides or saccharide derivatives as otherwise described herein. In exemplary embodiments, hydrophilic bulking agents can include oligofructose, dextrins, monosaccharides (e.g., fructose or glucose), disaccharides (e.g., palatinose or sucrose), hydrogenated carbohydrates, also known as sugar alcohols (e.g., polyols, monosaccharide alcohols, disaccharide alcohols, or oligosaccharide alcohols), and syrups (e.g., glucose syrup or fructose syrup). The hydrophilic bulking agent further may be a synthetic material, such as soluble fibers (e.g., polydextrose).

The hydrating materials used in the hydrocolloid system can include any variety of materials configured to donate water to the hydrophilic, long-chain polymer. The hydrating material particularly can be substantially pure water; however, the hydrating material may be an aqueous composition including one or more additives, such as a syrup, a fruit juice, or a flavoring liquid.

In some embodiments, a pH modifier particularly can be an acidifier. Non-limiting examples of acidic materials that may be used include citric acid, malic acid, lactic acid, tartaric acid, fumaric acid, phosphoric acid, ascorbic acid, sodium bisulphate, and combinations thereof.

The relative amount of the components utilized in a gummy composition can vary. The following embodiments exemplify the relative amounts of the components that may be utilized. All percentages are on a weight/weight basis (the weight of the specific component relative to the total weight of the gummy composition).

The gummy composition can comprise about 70% to about 94%, about 75% to about 90%, or about 78% to about 86% w/w of the hydrophilic bulking agent(s), particularly one or more saccharides or saccharide derivatives. Within the above ranges, the hydrophilic bulking agent(s) can comprise: about 1% to about 30%, about 5% to about 20%, or about 8% to about 18% w/w of one or more hydrogenated carbohydrates; about 10% to about 70%, about 15% to about 65%, or about 20% to about 60% w/w of sugar syrup solids; about 10% to about 70%, about 15% to about 65%, or about 20% to about 60% w/w of granular sugar.

The gummy composition can comprise about 1% to about 20%, about 1% to about 15%, or about 2% to about 7% w/w of the one or more hydrophilic, long-chain polymers.

The gummy composition can comprise about 5% to about 35%, about 10% to about 25%, or about 16% to about 22% w/w of water.

The gummy composition can comprise up to about 2%, up to about 1.5%, or up to about 1% w/w of a pH modifier. More particularly, about 0.1% to about 1%, about 0.2% to about 0.8%, or about 0.3% to about 0.6% w/w of the pH modifier can be used.

The gummy composition can comprise up to about 4%, up to about 2%, or up to about 1% of coloring agents.

The gummy composition can comprise up to about 4%, up to about 2%, or up to about 1% of flavoring agents.

In a non-limiting example, a gummy composition can comprise about 1% to about 4% by weight of pectin; 0% to about 3% by weight of further hydrophilic, long-chain polymers (e.g., starch, gelatin, carrageenan, cellulosic material, agar, or gelan); about 10% to about 70% by weight sugar syrup solids (e.g., glucose syrup solids); about 10% to about 70% by weight granular sugar (e.g., sucrose); about 0% to about 30% by weight of hydrogenated carbohydrates (e.g., sorbitol syrup, glycerol, mannitol, maltitol, erythritol, isomalt); about 0.1% to about 1.5% by weight citric acid (or other pH modifier); and the balance water, with weights being based on the total weight of the gummy composition.

The nature of the gummy composition used in forming the multicomponent dosage forms discussed herein can cause the dosage forms to be substantially chewable. A "chewable" dosage form, while capable of being swallowed whole, is configured specifically for chewing prior to swallowing. As such, a chewable dosage form is specifically distinguishable from a non-chewable dosage form, such as a vitamin tablet or capsule that is intended to be swallowed whole. In some embodiments, the term chewable can thus mean that the dosage form is intended to be retained in the mouth of the consumer for a period of time prior to swallowing during which time the dosage form may undergo a change in structure that facilitates ease of swallowing. The chewable dosage form may thus be reduced to smaller pieces through mastication. In some embodiments, the chewable dosage form may be configured to at least partially dissolve within the mouth of the consumer. As such, the chewable dosage form may also be dissolvable and may thus be referred to as a "melt-away" form.

The second composition used in the multicomponent dosage forms of the present disclosure can be provided in a variety of forms and combinations of materials. As such, the multicomponent dosage form can be configured as needed to achieve not only the desired delivery of one or more active ingredients but also to provide one or more desired organoleptic properties. For example, the second composition may be in a form such that it has a texture that is substantially different from the texture of the gummy composition or a form such that it has a texture that is substantially the same as the texture of the gummy composition. In one or more embodiments, the second composition (or one or more further compositions) may be provided in one or more of the following forms: crunchy or otherwise brittle; powdery; resilient; or chewy. Similarly, the second composition (or one or more further compositions) can have a taste that is complimentary or contrasting to the gummy composition. For example, where the gummy composition is typically sweet, the second composition may be substantially sour. A variety of flavor and taste combinations can be prepared in light of the present disclosure.

The second composition preferably is in the form of a solid material. The solid form is particularly maintained not only at standard room temperatures but also at elevated temperatures, such as up to about 100° C. in some embodiments. As such, the second composition specifically may not be in the form of a viscous fluid at such elevated temperatures.

In one or more embodiments, the second composition can be in the form of a particulate material. The term "particulate material" is intended to mean any material that is in the form of a plurality of individual particles of a typically small size, such as having an average size of about 0.5 mm or less, about 0.25 mm or less, or about 0.1 mm or less. Average particle size particularly can be in the range of about 0.1 m to about 0.5 mm, about 0.5 µm to about 0.25 mm, or about 1 m to about 0.1 mm. A particulate material can be in the form of a powder. A particulate material further encompasses granules, beads, pearls, prills, and other like forms.

In one or more further embodiments, the second composition can specifically be in a unit form, and the individual unit(s) may be pre-formed prior to combination with the gummy composition. Such pre-formed unit structure can be particularly useful to achieve compartmentalization of an active ingredient but can also be useful for ease of manufacturing of the multicomponent dosage forms. The second component thus may comprise a single, pre-formed solid unit or a plurality of pre-formed solid units. The unit or units can be in the form of any generally recognized oral dosage form, such as pharmaceutical dosage forms that are intended for oral administration. Non-limiting examples of solid dosage forms that are encompassed by the present disclosure include tablets, caplets, hard shell capsules, soft shell capsules, microcapsules, and pastilles. Any other solid forms suitable for oral administration are likewise encompassed. The pre-formed unit dosage form unit may be substantially homogeneous in composition throughout the unit. The pre-formed dosage form unit may include a coating (e.g., a coated tablet). The solid dosage form unit may be hollow (e.g., a gelatin capsule defining a hollow interior), and the hollow interior of the solid dosage form may be empty or may include one or more additives. The additive, for example, may be an active ingredient, may be a flavor, and/or may be a material designed to provide a specific sensation or organoleptic effect. Materials positioned within a hollow interior of a solid dosage unit can be in the form of a liquid, a solid unit, solid particles (including powders and beads), and/or microcapsules. A hollow, solid dosage unit may, for example, include a material that is intended to remain separated from another material in the multicomponent dosage form until administration. For example, the hollow, solid dosage unit may include a flavor that is intended to complement another flavor present in the multicomponent dosage form. Likewise, hollow, the solid dosage unit may include a material that is configured to react with another material in the multicomponent dosage form (which other material may likewise be included in a hollow, solid dosage unit). For example, an acidic material and a basic material may be included in the multicomponent dosage form, and one or both of the materials may be included in a hollow, solid dosage unit so that, upon chewing by a user, the two materials are combined to provide an effervescing effect. While the second component can include a liquid, the liquid preferably is contained within a solid unit (e.g., a shell or capsule) so that the solid unit effective separates the liquid from the outer gummy composition of the multicomponent dosage form.

The second composition is thus defined in some embodiments in relation to being a pre-formed unit. This allows for preparation of a wide variety of compositions that can include a great number of different materials to allow for the greatest variation in composition taste and organoleptic nature. As described in greater detail below, the pre-formed solid dosage units can be prepared in advance and stored for a desired length of time prior to combining the pre-formed solid units with the gummy composition to provide the final multicomponent dosage form.

The second composition specifically can be in a compressed form and thus be a compressed solid. The second composition preferably is solid at standard temperature and has a melting temperature of no lower than 40° C., no lower than 45° C., or no lower than 50° C. The compressed solid can be formed from a plurality of particles that can vary in size from fine powders to coarse beads or pellets. A compressed solid thus may be compacted to provide its final shape. The compressed solids may be prepared from a variety of materials and may take on a variety of configurations. While specific materials are further described herein, in one or more embodiments, compressed solids according to the present disclosure can comprise one or more saccharides, saccharide derivatives, lipids, cellulosic polymers, cellulosic polymer derivatives, and/or inorganic salts as major components thereof. It is understood, however, that specific compositions will comprise additional components.

In some embodiments, the second composition can be substantially in the form of a tablet, caplet, or the like. Although the term "tablet" is used, it is understood that the tablet can have a variety of shapes, such as being substantially spherical, cubed, or the like. In preferred embodiments, the tablets can be in the form of a compressed matrix comprising a mixture of materials.

In some embodiments, a second composition in a substantially tabletted form can comprise a compressible material of a nature and in an amount suitable to form a compressed matrix of desired hardness. For example, the tabletted composition can be compressed to a hardness of about 2 Kp to about 35 Kp. In some embodiments, the tabletted composition may be in a rapidly disintegrating form (i.e., under mouth conditions). In such embodiments, the tabletted composition may be compressed to a hardness of about 2 Kp to about 20 Kp, about 4 Kp to about 20 Kp, about 4 Kp to about 12 Kp, or about 4 Kp to about 8 Kp. In further embodiments, it may be desirable to provide a core with increased hardness that exhibits slower disintegration in the mouth of an individual. As such, the core may be compressed to a hardness of about 6 Kp to about 35 Kp, about 8 Kp to about 25 Kp, or about 10 Kp to about 20 Kp. The hardness may be as measured prior to combination with the gummy composition. Accordingly, the tablets can be formed to have a first hardness as defined above and be configured to reduce in hardness upon combination with the gummy composition, for example, in response to ingress of moisture from the gummy composition. If desired, the tablets can be configured to have a first hardness that facilitates ease of manufacturing and be configured to reduce in hardness after combination with the gummy composition such that chewing of the gummy composition causes the tablet to substantially disintegrate as opposed to requiring fracturing during chewing. Such characteristics can be modified as desired.

Discussion herein of "mouth conditions" can relate to one or more characteristics (in any combination) associated with the presence of an item in the mouth of an individual. For example, mouth conditions can include any combination of temperature, moisture, and pH typically found in the mouth of a human as well as the shear, compression, and other mechanical forces that may be applied by the teeth during chewing. Mouth conditions particularly can relate to being in contact with saliva. In some embodiment, mouth conditions can particularly mean contact with saliva at the temperature and pH typically present in the human mouth.

The tablet composition can comprise as a major component a carrier material. The carrier material may particularly be a compressible material, and a single carrier material or a plurality of different carrier materials can be used. For example, in some embodiments, a carrier material can be selected from the group consisting of saccharides, saccharide derivatives, inorganic salts, and combinations thereof. Beneficially, such materials may also be compressible so as to be useful in forming a compressed structure, as further described herein. A carrier may also be characterized as a bulking agent, and examples of materials below for use as a carrier may also be used in one or more embodiments as a bulking agent.

A tablet in some embodiments may be compressed to form a solid monolith. In some embodiments, a monolithic structure need not necessarily be compressed but may be prepared by any method wherein a substantially continuous structure is formed.

The term "saccharide" as used herein (including in relation to all compositions described herein) can encompass sugar, starch, and cellulose materials. A saccharide can be a monosaccharide, a disaccharide, an oligosaccharide, or a polysaccharide. Exemplary monosaccharides include glucose, fructose, and galactose. Exemplary disaccharides include sucrose, lactose, lactulose, maltose, trehalose, cellobiose, and chitobiose. Exemplary oligosaccharides include fructo-oligosaccharides, galactooligosaccharides, and mannan oligosaccharides. Exemplary polysaccharides include glucans, starches, celluloses, pectins, xylans, arabinoxylans, mannans, and galactomannans. Saccharide derivatives can include any material that is derived from a saccharide. In particular, saccharide derivatives may be formed by substitution of one or more hydroxyl groups on the compound to form, for example, amino sugars, acidic sugars, deoxy sugars, sugar alcohols, glycosylamines, and sugar phosphates. Non-limiting examples of sugar alcohols include erythritol, xylitol, ribitol, mannitol, sorbitol, volemitol, isomalt, maltitol, and lactitol. Saccharide derivatives can also encompass artificial sweeteners, such as sucralose.

In some embodiments, carrier materials can include one or more of the following: sucrose, fructose, lactose, maltose, mannitol, xylitol, maltitol, sorbitol, hydrogenated starch hydrosylate, maltodextrin, cellulose, microcrystalline cellulose, hydroxypropyl cellulose, hydroxypropylmethyl cellulose, hydroxyethyl cellulose, starch, pre-gelatinized starch, dicalcium phosphate, guar gum, carboxymethylcellulose (and salts thereof—e.g., sodium salts), polyethylene oxide, polyethylene glycol (and co-polymers thereof—e.g., poloxamer/PLURONIC®).

Disintegrants are understood in the art to be materials that facilitate the de-aggregation of a compressed dosage form under desired conditions, such as in one or more areas along the gastrointestinal tract, which can be effective to facilitate release of an active agent at one or more desired locations. Any material recognized as a disintegrant may be used in the present core compositions. Non-limiting examples of disintegrants that may be used include croscarmellose sodium, crospovidone (i.e., crosslinked polyvinyl pyrrolidone), polyvinyl acetate, silica, and sodium starch glycolate.

A tablet composition according to the present disclosure can also include further components. For example, various processing aids may be included. Non-limiting examples of processing aids include magnesium stearate, stearic acid, glyceryl monostearate, sodium stearyl fumerate, talc, silicon dioxide, polyvinylpyrrolidone (povidone), polyvinyl alcohol, and hydroxypropylmethyl cellulose. Processing aids may be any material recognized in the art as a lubricant in a tableting process, as a glidants to aid powder flow, or a binder to aid powder granulation.

A tablet composition further may include one or more agents adapted to modify, particularly improve, the organoleptic properties of the tablet composition. For example taste-making agents may be utilized. Non-limiting examples of taste-masking agents include cyclodextrins and ion exchange resins. Further, flavoring agents may be utilized.

Non-limiting examples of flavoring agents include citric acid, tartaric acid, confectionary sugars, artificial sweeteners (e.g., acesulfame potassium, aspartame, neotame, saccharine, and sucralose), salts (e.g., sodium chloride), plant extracts (e.g., vanilla, luo han guo), and essential oils.

The second composition, according to one or more embodiments, may be characterized as being an orally disintegrating tablet (ODT), a fast melt or quick melt dosage form, or an orodispersible dosage form. In some embodiments, the tablet can be in a rapidly disintegrating form. As used herein, rapid disintegration can be defined as achieving substantially complete disintegration under mouth conditions in a time of less than 20 seconds, less than 15 seconds, or less than 10 seconds. This can be calculated as the time from which the tablet becomes exposed to the mouth conditions. For example, when the tablet is completely surrounded by an outer gummy composition, the time to disintegration can be calculated from time when the tablet becomes exposed through at least partial removal of the outer gummy composition, such as through chewing and/or dissolving of the gummy composition. Substantially complete disintegration can mean de-aggregation, dispersion, or dissolution of the core to an extent that no portion of the core remains as a solid monolith compact having a size that is greater than 50%, greater than 10%, greater than 5%, or greater than 2% of the size of the original core.

A rapidly disintegrating tablet composition in some embodiments may have an initial size wherein a maximum dimension thereof is about 6 mm to about 12 mm. In some embodiments, the rapidly disintegrating tablet composition may be defined by a diameter and a thickness. For example, the rapidly disintegrating tablet composition can have a diameter of about 6 mm to about 12 mm, about 7 mm to about 12 mm, or about 8 mm to about 12 mm, and the rapidly disintegrating tablet composition can have a thickness of about 0.5 mm to about 8 mm, about 1 mm to about 6 mm, or about 2 mm to about 6 mm.

When the multicomponent dosage form is substantially in a core/shell configuration (e.g., wherein the outer gummy composition is completely surrounding one or more cores, the overall dosage form can have a maximum outer dimension of about 10 mm to about 35 mm. In some embodiments, the dosage form can have a diameter, length, or width of about 10 mm to about 35 mm, about 12 mm to about 32 mm, or about 15 mm to about 30 mm, and the dosage form can have a thickness of about 10 mm to about 30 mm, about 10 mm to about 25 mm, or about 10 mm to about 20 mm.

In one or more embodiments, the dimensions of a core composition within a gummy composition can vary relative to the dimensions of the gummy composition. In particular, it has been found that overall product characteristics can be improved by maintaining a minimum "shell" thickness. Specifically, it can be desirable for the thickness of the gummy composition shell (measured as the distance from the outer surface of the core composition to the outer surface of the gummy composition) to be about 1.5 mm or greater, about 2 mm or greater, or about 2.5 mm or greater, such as about to about 1.5 mm to about 10 mm or about 2 mm to about 8 mm. Such thickness specifically can apply to all points of the shell surrounding the core composition. The gummy shell thickness need not necessarily be constant at all points so long as the minimum shell thickness is met at all point of the gummy shell.

When a core/shell configuration is used, the multicomponent dosage form can include only a single core. In some embodiments, though, a plurality of cores, each of the same composition or of different compositions, may be included.

For example, in some embodiments, the multicomponent dosage form can comprise an outer gummy composition shell surrounding a single core formed of the second composition (e.g., in a tablet form or in a different form as otherwise described herein). In other embodiments, the multicomponent dosage form can comprise an outer gummy composition surrounding two or more cores, which cores may all be formed of the same composition or may be formed of two or more different compositions. When a plurality of cores is used, less than all of the cores may be rapidly disintegrating. Moreover, the plurality of cores may have different sizes. Regardless of core number and dimensions, it is preferably for the minimum gummy shell thickness as discussed above to be maintained at all points in the gummy shell.

Shapes and sizes of the tablet composition as provided above are understood to be exemplary in nature and not limiting of the present disclosure. In some embodiments, for example, a unit formed a composition that is different from the gummy composition may be in a substantially non-tableted form. Exemplary embodiments of non-tablet unit forms include wafers and films. Moreover, the units formed of the second composition may be freeze-dried and may be present as a single mass or as particulates. In some embodiments, nanoparticles and/or microparticles may be used. Microparticles can have an average diameter of about 1 micron to about 1,000 microns, about 5 microns to about 750 microns, or about 10 microns to about 500 microns. Nanoparticles can have an average diameter of about 5 nm to about 1,000 nm, about 10 nm to about 900 nm, or about 50 nm to about 750 nm.

The relative amount of the components utilized in forming a rapidly disintegrating composition can vary. The following embodiments exemplify the relative amounts of the components that may be utilized. All percentages are on a weight/weight basis (the weight of the specific component relative to the total weight of the composition).

A rapidly disintegrating tablet composition (or other form for combination with a gummy composition to form the multicomponent dosage form) can comprise about 5% to about 80%, about 25% to about 80%, or about 40% to about 80% w/w of a carrier material, which particularly can be a compressible material, including one or more saccharides or saccharide derivatives and/or one or more inorganic salts. In some embodiments, a rapidly disintegrating tablet composition can comprise greater than 50%, greater than 55%, or greater than 60% w/w of the carrier material or materials.

A rapidly disintegrating tablet composition can comprise about 0.1% to about 15%, about 1% to about 10%, or about 3% to about 8% w/w of a disintegrant.

A rapidly disintegrating tablet composition can comprise about 0.1% to about 60%, about 1% to about 55%, or about 5% to about 50% w/w of active ingredient(s).

A rapidly disintegrating tablet composition can comprise about 0.1% to about 10%, about 0.2% to about 5%, or about 0.5% to about 3% w/w of one or more processing aids.

A rapidly disintegrating tablet composition can comprise up to about 4%, up to about 2%, or up to about 1% w/w of flavoring agents and/or taste masking agents (e.g., about 0.01% to about 4%, about 0.05% to about 2%, or about 0.1% to about 1% w/w).

In some embodiments, one or more of the materials used in forming a rapidly disintegrating tablet composition can be hydrophilic. For example, a hydrophilic carrier material can be used, particularly a carrier material that allows for the light compressibility needed to form the tablet. The use of a hydrophilic carrier can improve tablet stability since the hydrophilic carrier may permit rapid water ingress but have a low equilibrium water content such that the amount of water that is absorbed into the tablet reaches a plateau without causing deliquescence of the tablet.

In some embodiments, a composition to be combined with a gummy composition to provide a multicomponent dosage form may be characterized as being in the form of mini-tablets ("minitabs"). A minitab may, in some embodiments, be considered to be in a rapidly disintegrating form. Alternatively, a minitab may be disintegrating but may undergo such process as a slower rate than otherwise described above. As such, a minitab may have a greater hardness than a rapidly disintegrating tablet. Whereas hydrophilic excipients may be useful in a rapidly disintegrating tablet, a minitab may benefit from the use of hydrophobic excipients. In particular, hydrophobic excipients can function to reduce the potential for water ingress and additionally have a low equilibrium water content such that the amount of water that is absorbed into the minitab reaches a plateau without causing stability issues within the minitab. If desired, however, hydrophilic excipients may likewise be used in a minitab.

A minitab can be fracturable and thus can be characterized in relation to a brittleness index of the core, typically in the range of 0.05 to 1.0. The brittleness index value may be as measured before combination with the gummy composition, as it is understood that, in some embodiments, the brittleness index may change after combination with the gummy composition. Preferably, the brittleness index value prior to combination with the gummy composition can be about 0.1 to about 0.99, about 0.2 to about 0.98, about 0.25 to about 0.97, or about 0.5 to about 0.95.

A minitab may have an initial size wherein a maximum dimension thereof is about 2 mm to about 10 mm. In some embodiments, a minitab composition may be defined by a diameter and a thickness. For example, the minitab composition can have a diameter of about 2 mm to about 10 mm, about 2 mm to about 6 mm, or about 3 mm to about 4 mm, and the minitab composition can have a thickness of about 0.5 mm to about 6 mm, about 1 mm to about 5 mm, or about 3 mm to about 4 mm. A multicomponent dosage form including one or more minitab compositions can have overall dimensions as already noted above.

The number and nature of minitabs utilized in an oral, chewable dosage form can be substantially as otherwise described above. In embodiments wherein a minitab composition is utilized, it can be beneficial to include a plurality of cores. For example, an oral, chewable dosage form of the present disclosure can include 2 to 20, 2 to 15, or 2 to 10 minitabs surrounded by an outer gummy composition. Each of the plurality of minitabs can have the same size or can be of different sizes and/or of different composition.

The use of the term "minitab" is meant to be descriptive and not necessarily limiting of the shape thereof. As already described above, a minitab can be substantially in the shape of a tablet, a sphere (or bead), spheroid, cube, wafer, film, or other like shape.

The relative amount of the components utilized in forming a minitab composition can vary. The following embodiments exemplify the relative amounts of the components that may be utilized. All percentages are on a weight/weight basis (the weight of the specific component relative to the total weight of the minitab composition).

A minitab composition can comprise about 15% to about 90%, about 25% to about 90%, or about 50% to about 90% w/w of a carrier material. In some embodiments, the carrier material may be a compressible material and may also include a hydrophilic diluent. The total amount of the carrier material may be selected from the group of saccharides or saccharide derivatives and/or inorganic salts. In some embodiments, a minitab composition can comprise greater than 50%, greater than 55%, or greater than 60% w/w of the carrier material or materials. In further embodiments, a minitab composition can comprise about 5% to about 80% or about 40% to about 80% w/w of a compressible material and can comprise about 10% to about 60% or about 20% to about 50% w/w of a hydrophilic diluent.

A minitab composition can comprise about 0.1% to about 15%, about 1% to about 10%, or about 3% to about 8% w/w of a disintegrant.

A minitab composition can comprise about 0.1% to about 60%, about 1% to about 55%, or about 5% to about 50% w/w of active ingredient(s).

A minitab composition can comprise about 0.1% to about 10%, about 0.2% to about 5%, or about 0.5% to about 3% w/w of one or more processing aids.

A minitab composition can comprise up to about 4%, up to about 2%, or up to about 1% w/w of flavoring agents and/or taste masking agents (e.g., about 0.01% to about 4%, about 0.05% to about 2%, or about 0.1% to about 1% w/w).

In one or more embodiments, the second composition can be in a form exhibiting specific textural properties. For example, the second composition can be provided in a pre-formed unit that exhibits chewiness or has a chewy texture. As would be understood in the art, a unit form having such texture would require repeated chewing within the mouth of a consumer in order to reduce the unit to pieces suitable for ease of swallowing. This is distinguishable from a unit that dissolves or is reduced substantially to a power or particulate form with little or no chewing. A chewy texture can be substantially matched to the texture of the gummy composition or may exhibit differing qualities. Embodiments of multicomponent dosage forms including a second composition substantially in the form of a chew can likewise be compressed solids and can be configured as otherwise described herein (e.g., core/shell; side-by-side; partially surrounded; etc.).

In one or more embodiments, a second composition substantially in the form of a chew can comprise one or more carriers, one or more hydrophilic polymers, and optionally one or more active ingredients. In some embodiments, one or more disintegrants may be included to provide the chewiness in an acceptable range for ease of consumption and/or for textural matching with the gummy composition. Likewise, lubricants and/or hydrophobic diluents and/or processing aids may be included to modify the texture as desired.

In some embodiments, a second composition substantially in the form of a chew can be compressed to a hardness of about 2 Kp to about 30 Kp, about 6 Kp to about 20 Kp, or about 10 Kp to about 18 Kp. A chewy form may also be characterized in relation to elasticity. For example, a chewy form may exhibit elastic or viscoelastic properties, particularly when in a hydrated form.

A composition prepared to be in a chewy form can comprise about 10% to about 60%, about 12% to about 50%, or about 15% to about 45% w/w of the one or more bulking agents (e.g., one or more saccharides or saccharide derivatives or other equivalent materials otherwise described herein). A chewy composition also can comprise about 5% to about 60%, about 10% to about 50%, or about 15% to about 45% w/w of the one or more hydrophilic polymers. One or more processing aids may be present in an amount of about 0.05% to 5% w/w. In some embodiments, a composition in a chewy form can include one or more active agents in an amount of 0.1% to about 60%, about 1% to about 55%, or about 5% to about 50% w/w.

In an exemplary embodiment, a multicomponent dosage form may include a composition in a chewy form having the following composition: about 10% to about 60% w/w of the one or more bulking agents, about 5% to about 60% w/w of the one or more hydrophilic polymers, about 0.05% to about 5% of one or more processing aids, and about 0.1% to about 60% w/w of the one or more active ingredients In a further exemplary embodiment, a multicomponent dosage form may include a composition in a chewy form having the following composition: about 20% to about 60% w/w of one or more bulking agents, about 20% to about 60% w/w of the one or more hydrophilic polymers, about 0.1% to 3% of one or more processing aids, and about 1% to about 40% w/w of one or more active ingredients.

In one or more embodiments, a multicomponent dosage form according to the present disclosure can include a second composition that is configured to provide a soft and/or smooth and/or rich texture. Such characteristics can, for example, be provided through use of a lipidic medium including, but not limited to, oils, fats, and compositions formed therewith.

Such characteristics also may be provided through use of one or more fat substitutes, such as various polyols (e.g., glycerol). The disclosure thus further encompasses pre-formed units of lipidic (of lipid-based) compositions.

Lipid-based compositions (and compositions exhibiting similar properties) can exist in a molten phase, a solid phase, or a semi-solid phase, and the transition between the phases can be achieved at temperatures wherein the lipid-based composition can provide specific textural properties. Lipid-based compositions, however, can be formed in one or more embodiments via compression or similar molding techniques. For example, the lipid-based composition can be a soft solid at typical room temperatures but be substantially resistant to melting at higher temperatures to facilitate manufacturing. In other words, the lipid-based compositions can have transition temperatures so that the composition will remain substantially solid while being combined with a heated gummy composition. The lipid based compositions can be configured to be a substantially homogeneous mixture of the lipid and the further ingredients. For example, solids may be homogeneously dispersed in the lipid base.

Suitable lipidic materials for use in forming such compositions include fats derived from vegetables, nuts, seeds, and the like. Non-limiting examples of suitable lipidic materials include fats derived from one or more of the following: cocoa, almonds, cashews, hazelnuts, macadamia nuts, peanuts, pecans, pistachios, walnuts, pumpkin seeds, sesame seeds, soybeans, rapeseed, corn, safflower seeds, and the like. Lipid based compositions can comprise a lipidic material in an amount of about 10% to about 60%, about 12% to about 55%, or about 15% to about 50% w/w. Specific, non-limiting examples of lipid based materials that may be used in preparing a composition as described herein include chocolates with any cocoa concentration (e.g., milk chocolate, dark chocolate, white chocolate), peanut butter, and the like. Such materials typically will include additional components, such as sugar, salt, other oils, and the like.

Compositions with a lipid base can include one or more further components. For example, one or more dairy components may be utilized, including fats, proteins, and/or sugars derived from cow milk, goat milk, and the like.

In one or more embodiments, the lipid based composition can include one or more bulking agents as described, particularly on or more saccharides or saccharide derivatives. For example, the composition can comprise about 10% to about 60%, about 12% to about 55%, or about 15% about 50% w/w of the one or more bulking agents.

The lipidic composition can comprise one or more active ingredients. For example, active ingredients may be present in concentration of about 0.1% to about 60%, about 1% to about 55%, or about 5% to about 50% w/w.

The compositions may likewise include a component of solids (i.e., which remain solid at temperatures above the melting temperature of the lipid used as the base material). Active ingredients may be solids present in the composition. Cocoa solids, milk solids, nut solids, seed solids, and the like are further examples of solids that may be present.

A lipidic composition can take on a variety of forms. For example, the composition may be a dispersion, an emulsion, a solution, a mixture, or the like. In some embodiments, the composition may include one or more ingredients useful to stabilize the composition and/or facilitate formation of a substantially homogeneous state. Emulsifiers (e.g., lecithin, monoglycerides, and the like) may be used, and suitable emulsifiers that are generally recognized as safe for products consumed by humans can be found in 21 CFR 178.3400.

Lipid based compositions can be made directly into the final form for combination with the gummy composition. In some embodiments, a mass of the lipid based composition can be formed as a solid and then granulated. The particulate material may then be compressed into a final desired shape (e.g., pellets) or plasticized, such as by low shear mixing of the material. In some embodiments, the lipid based material may be provided in a molten condition and molded into specific forms or shapes.

Lipid based compositions can be particularly useful as carriers for active agents that may be prone to degradation if provided in other types of compositions. For example, beneficial bacteria that are water sensitive may be substantially enclosed in a lipid based composition so as to remain active until consumer ingestion. Likewise, heat and/or light sensitive active agents may benefit from being present in the lipid based composition, which can be provided in a substantially opaque color and which can be formed under conditions with significantly cooler temperatures compared to the manufacture of a gummy composition. Water reactive chemicals (e.g., bicarbonate) also can benefit by being provided within the hydrophobic, lipid based composition.

Units in a chewy or lipid based from for use in a multicomponent dosage of the present disclosure can have a variety of sizes. Such units, for example, can have a maximum dimension of about 1 mm to about 12 mm, about 2 mm to about 10 mm, or about 3 mm to about 8 mm. In some embodiments, the unit can be substantially spherical, and the noted maximum dimension can be a diameter of the unit. In other embodiments, the unit can have a maximum dimension as noted (e.g, a length or width) and can have a thickness that is less than the maximum dimension. For example, the unit can have a length or width as noted above, and have a thickness that is about 10% to about 95%, about 15% to about 85%, or about 25% to about 75% of the maximum dimension.

In one or more embodiments, the second component can be a solid shell that defines a hollow interior. Non-limiting examples of solid shell dosing units include hard gelatin capsules and soft gelatin capsules. The solid shell itself may include an active ingredient. An active ingredient may be included in the hollow interior of the solid shell. The hollow interior additionally, or alternatively, may include any one or more of a variety of compositions, including flavors, materials providing warming sensations, materials providing cooling sensations, materials providing tingling sensations, and materials configured to react with other materials in the multicomponent dosage form to provide an specific organoleptic sensation.

In one or more embodiments, the multicomponent dosage forms of the present disclosure can be particularly beneficial in light of the good stability provided by the second compositions that make them particularly suitable for combination with the gummy compositions. Good stability can be useful where the second composition includes an active ingredient. Such improved stability can be characterized in some embodiments in relation to the ability of the core composition to resist water absorption. Such stability of the presently disclosed core compositions is illustrated in the Examples appended hereto. Test conditions for evaluating stability in relation to resisting water absorption are found in Guidance for Industry Q1A(R2) Stability Testing of New Drug Substances and Products (November 2003, Revision 2), which guidelines are established by the U.S. Department of Health and Human Services, Food and Drug Administration, Center for Drug Evaluation and Research (CDER), and Center for Biologics Evaluation and Research (CBER).

In some embodiments, compositions in the form of a tablet, minitab, or the like as described herein can exhibit a particularly level of stability as measured separate from a gummy composition. For example, a tabletted composition can be water stable such that, separate from another composition (e.g., separate from a gummy composition), the tabletted composition absorbs less than about 5% by weight of water (based on the weight of the tabletted composition) over a time of 14 days at a temperature of 40° C. and a relative humidity of 75%. Such stability exemplifies the ability of the tabletted composition to resist water uptake from the gummy composition when the tabletted composition is combined with the gummy composition particularly, for example, in embodiments wherein one or more tabletted compositions may be present as one or more cores surrounded by a gummy outer layer or shell. Stability can also relate to the ability of the tabletted composition to resist degradation in relation to an active ingredient included therein. In some embodiments, for example, a tabletted composition can be stable such that the active ingredient exhibits substantially no degradation when the tabletted composition is stored for a time of 20 days at a temperature of 40° C. and a relative humidity of 75%.

Compositions in that are substantially in the form of a chew likewise can exhibit good stability. For example, a chewy composition as described herein can be water stable such that, separate from another composition (e.g., separate from a gummy composition), the chewy composition absorbs less than about 10% by weight of water (based on the weight of the chewy composition) over a time of 5 days at a temperature of 40° C. and a relative humidity of 75%. As above, chewy compositions as described herein also can be useful as stable carriers for active ingredients. For example, a chewy composition as described herein can be stable such that the active ingredient in the chewy composition exhibits substantially no degradation when the chewy composition is stored for a time of 11 days at a temperature of 40° C. and a relative humidity of 75%.

Still further, lipid based compositions as described also can provide good stability, particularly in relation to maintaining the integrity of an active ingredient. For example, in some embodiments, a lipid based composition as described herein can be stable such that, after being stored for a time of 28 days at a temperature of 25° C. and a relative humidity of 60%, the lipid based composition comprises less than about 0.1% by weight of active ingredient degradation products relative to the weight of the active ingredient. In further embodiments, the lipid based composition can be stable such that, after being stored for a time of 28 days at a temperature of 50° C. and a relative humidity of 60%, the lipid based composition comprises less than about 2% by weight of active ingredient degradation products relative to the weight of the active ingredient.

The use of multiple compositions for delivery of an active ingredient can be particularly beneficial in that a variety of tastes and organoleptic characteristics can be provided while simultaneously providing for stability of the active ingredient. In some embodiments, stability of one or more elements of a multicomponent dosage form may be increased through inclusion of a barrier element. Such barrier element can particularly be adapted to minimize the ingress/migration of water from one composition to the other composition (e.g., from the gummy composition into the second composition that may be in physical contact with the gummy composition and particularly may be at least partially surrounded by the gummy composition. This can be particularly beneficial to improve stability in long-term storage. The barrier element may be present as one: or more intermediate layers configured to compartmentalize a unit of one composition (e.g., a core) from the gummy composition (e.g., a shell).

A barrier layer may partially surround, substantially surround, or completely surround a unit of a composition as described herein. For example, a tablet, a chew, or a lipid based composition may be partially, substantially, or completely separated from a gummy composition via a barrier component. In some embodiments, a plurality of barrier components (e.g., layers or films) may be used.

Figure 9:
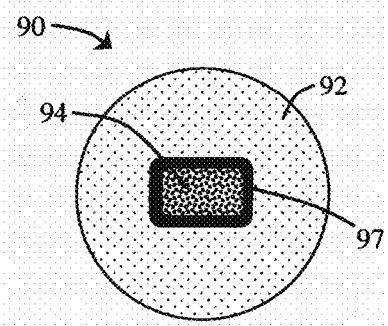
FIG. 9 is a cross-section of a multicomponent composition according to an exemplary embodiment of the present disclosure illustrating a gummy composition surrounding a second composition that is separated from the gummy composition with a barrier layer.

FIG. 9 illustrates a multicomponent: dosage form 90 that comprises a gummy composition 92, which is substantially a shell surrounding a second composition 94, which is substantially a core. The second composition 94 is separated from the gummy composition 92 with a barrier 97 that functions substantially as a layer that separates the gummy composition from the second composition to substantially prevent or completely prevent water ingress from the gummy composition to the second composition. Likewise, returning to FIG. 6, one or both of layer 63 and layer 65 may function as a barrier in this regard. An intermediate layer may be utilized as a barrier around each individual core that may be present in a multicomponent dosage form. In other embodiments, two or more of a plurality of cores present in a multicomponent dosage form may be substantially surrounded by a single barrier element.

In some embodiments, further compartmentalization of the active ingredient(s) may be provided. For example, in addition to separating the active ingredient from the gummy composition by providing the active ingredient in a separate composition, the active ingredient may also be in an encapsulated form. Alternatively, the entire composition in which the active ingredient is included may be in an encapsulated form. For example, a composition including the active ingredient may be provided substantially in a unit form as described herein, may be in particulate form, may be in the form of microparticles or nanoparticles, and the composition may be encapsulated (e.g., encapsulated chews, encapsulated lipid based units, encapsulated minitabs, encapsulated particles, encapsulated microparticles, or encapsulated nanoparticles).

Active ingredients and/or compositions including active ingredients may be encapsulated utilizing any encapsulating technology known in the art. For example, microcapsules can be formed using any of various chemical encapsulation techniques such as solvent evaporation, solvent extraction, organic phase separation, interfacial polymerization, simple and complex coacervation, in-situ polymerization, liposome encapsulation, and nanoencapsulation. Alternatively, physical methods of encapsulation could be used, such as spray coating, pan coating, fluid bed coating, annular jet coating, spinning disk atomization, spray cooling, spray drying, spray chilling, stationary nozzle coextrusion, centrifugal head coextrusion, or submerged nozzle coextrusion.

Regardless of the encapsulation methodology employed, the outer wall or shell material and solvents used to form the capsules can vary. Classes of materials that are typically used as wall or shell materials include proteins, polysaccharides, starches, waxes, fats, natural and synthetic polymers, and resins. Exemplary materials for use in the microencapsulation process used to form the microcapsules include gelatin, acacia (gum arabic), polyvinyl acetate, potassium alginate, carob bean gum, potassium citrate, carrageenan, potassium polymetaphosphate, citric acid, potassium tripolyphosphate, dextrin, polyvinyl alcohol, povidone, dimethylpolysiloxane, dimethyl silicone, refined paraffin wax, ethylcellulose, bleached shellac, modified food starch, sodium alginate, guar gum, sodium carboxymethylcellulose, hydroxypropyl cellulose, sodium citrate, hydroxypropylmethylcellulose, sodium ferrocyanide, sodium polyphosphates, locust bean gum, methylcellulose, sodium trimetaphosphate, methyl ethyl cellulose, sodium tripolyphosphate, microcrystalline wax, tannic acid, petroleum wax, terpene resin, tragacanth, polyethylene, xanthan gum, and polyethylene glycol.

Microcapsules are commercially available, and exemplary types of microcapsule technologies are of the type set forth in Gutcho, Microcapsules and Microencapsulation Techniques (1976); Gutcho, Microcapsules and Other Capsules Advances Since 1975 (1979); Kondo, Microcapsule Processing and Technology (1979); Iwamoto et al., AAPS Pharm. Sci. Tech. 2002 3 (3): article 25; U.S. Pat. No. 5,004,595 to Cherukuri et al.; U.S. Pat. No. 5,690,990 to Bonner; U.S. Pat. No. 5,759,599 to Wampler et al.; U.S. Pat. No. 6,039,901 to Soper et al.; U.S. Pat. No. 6,045,835 to Soper et al.; U.S. Pat. No. 6,056,992 to Lew; U.S. Pat. No. 6,106,875 to Soper et al.; U.S. Pat. No. 6,117,455 to Takada et al.; U.S. Pat. No. 6,482,433 to DeRoos et al.; and U.S. Pat. No. 6,929,814 to Bouwmeesters et al.; each of which is incorporated herein by reference.

Embodiments of the present disclosure are further illustrated by the following examples, which are set forth to illustrate the presently disclosed subject matter and are not to be construed as limiting. The examples describe exemplary formulations for rapidly disintegrating core compositions and exemplary formulations for minitab core compositions. The examples further describe stability testing for the core compositions. The examples also provide exemplary formulations for gummy bases useful as the outer composition surrounding a core.

Example 1—Rapidly Disintegrating Tablet Compositions

Exemplary formulations according to the present disclosure for rapidly disintegrating tablet compositions are shown in TABLE 1 and TABLE 2. Each exemplary tablet was prepared to include 80 mg of acetaminophen as the active ingredient using 86.96 mg of ACTIMASK® acetaminophen. The LUDIFLASH® used in formulation 14CF13/042 is co-processed mannitol, crospovidone, and polyvinyl acetate. The PEARLITOL® Flash used in formulation 14CF13/043 is co-processed mannitol and starch. The PHARMABURST® 500 used in formulation 14CF13/044 is co-processed mannitol, sorbitol, crospovidone, and silica combined with aspartame and magnesium stearate. The PROSOLV® ODT used in formulation 14CF13/045 is co-processed microcrystalline cellulose, colloidal silicon dioxide, mannitol, fructose, and crospovidone.

To prepare each formulation, the compressible carrier was weighed and screened before being placed into a blending vessel (Turbula T2F blender). The active ingredient was added to the blending vessel, and the components were blended for 10 minutes. The sodium stearyl fumarate lubricant was added to the blended components while sifting through a 500 μm sieve, and the mixture was blended for 2 minutes. The final mixture was compressed using a Manesty F single station tablet press to the target tablet weight and hardness.

TABLE 1

| Ingredient | Function | mg/tablet (% w/w) Formulation Number | | | |
|---|---|---|---|---|---|
| | | 14CF13/042 | 14CF13/043 | 14CF13/044 | 14CF13/045 |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) |
| LUDIFLASH ® | Compressible carrier | 210.4 mg (70% w/w) | — | — | — |
| PEARLITOL ® Flash | Compressible carrier | — | 210.4 mg (70% w/w) | — | — |
| PHARMABURST ® 500 | Compressible carrier | — | — | 210.4 mg (70% w/w) | — |
| PROSOLV ® ODT | Compressible carrier | — | — | — | 210.4 mg (70% w/w) |
| Sodium Stearyl Fumarate | Lubricant | 3.0 mg (1% w/w) | 3.0 mg (1% w/w) | 3.0 mg (1% w/w) | 3.0 mg (1% w/w) |

TABLE 2

| Ingredient | Function | mg/tablet (% w/w) Formulation Number | | | | |
|---|---|---|---|---|---|---|
| | | 14CF13/046 | 14CF13/047 | 14CF13/048 | 14CF13/049 | 14CF13/050 |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) | 86.96 mg (29% w/w) |
| Mannitol | Compressible carrier | 180.04 mg (60% w/w) | 180.04 mg (60% w/w) | 180.04 mg (60% w/w) | 180.04 mg (60% w/w) | 180.04 mg (60% w/w) |
| Croscarmellose sodium | Disintegrant | 30.0 mg (10% w/w) | — | — | — | 15.0 mg (5% w/w) |
| Sodium starch glycolate | Disintegrant | — | 30.0 mg (10% w/w) | — | — | 15.0 mg (5% w/w) |
| Crospovidone | Disintegrant | — | — | 30.0 mg (10% w/w) | — | — |
| Crospovidone (super fine) | Disintegrant | — | — | — | 30.0 mg (10% w/w) | — |
| Sodium Stearyl Fumarate | Lubricant | 3.0 mg (1% w/w) | 3.0 mg (1% w/w) | 3.0 mg (1% w/w) | 3.0 mg (1% w/w) | 3.0 mg (1% w/w) |

Example 2—Weight Stability of Rapidly Disintegrating Tablet Compositions

The formulations shown in TABLE 1 and TABLE 2 were weighed at the time for tablet formation. The tablets were stored in open conditions at a temperature of 40° C. and a relative humidity of 75% for 14 days. The tablets were weighed, and the percent change in weight was recorded, with any increase in weight being attributed to uptake of ambient water.

Figure 10:
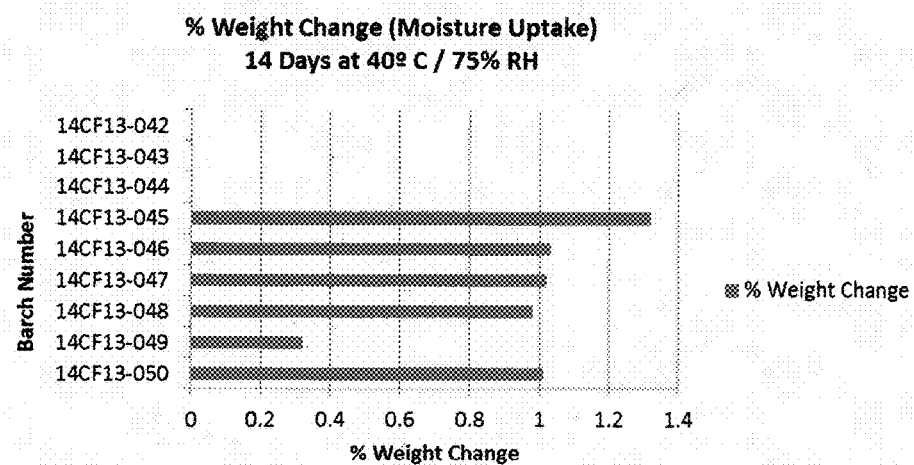
FIG. 10 is a graph showing the percent weight change (moisture uptake) of exemplary tabletted compositions according to the present disclosure when subject to storage for 14 days at 40° C. and 75% relative humidity.

The results are provided in FIG. 10. As seen therein the tablets on average exhibited a water weight gain of less than 1.4%. Formulations 14CF13/042 and 14CF13/043 demonstrated no weight gain while formulation 14CF13/044 disintegrated within 5 days.

Example 3—Chemical Degradation Analysis of Acetaminophen

Formulations 14CF13/042, 14CF13/073, 14CF13/049, and 14CF13/050 were evaluated by high performance liquid chromatography (HPLC) after open storage for 20 days at a temperature of 40° C. and 75% relative humidity. The samples were tested against tablets of identical formulation stored under lab conditions which are typically 20-25° C. and 55-65% relative humidity. The lab stored tablets were controls for the samples that were stored open at the stress storage condition of 40° C./75% RH In all four samples, no degradation was observed in that the chromatogram for the openly stored sample was identical to the chromatogram for the lab-stored tablet.

Example 4—Minitab Compositions

Exemplary formulations according to the present disclosure for minitab compositions are shown in TABLE 3 and TABLE 4. Each exemplary tablet was prepared to include 80 mg of acetaminophen as the active ingredient using 86.96 mg of ACTIMASK® acetaminophen. To prepare each formulation, all ingredients except the API and the lubricant were weighed and screened before being placed into a blending vessel (Turbula T2F blender). The active ingredient was added to the blending vessel, and the components were blended for 10 minutes. The lubricant was added to the blended components while sifting through a 500 μm sieve, and the mixture was blended for 2 minutes. The final mixture was compressed using a Manesty F single station tablet press to the target tablet weight and hardness.

TABLE 3

| Ingredient | Function | 14CF20/005 mg/tablet (% w/w) | 14CF20/006 mg/tablet (% w/w) | 14CF20/007 mg/tablet (% w/w) | 14CF20/008 mg/tablet (% w/w) |
| --- | --- | --- | --- | --- | --- |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) |
| Sorbitol | Compressible carrier | 210.04 mg (70% w/w) | — | — | — |
| Mannitol | Compressible carrier | — | 210.04 mg (70% w/w) | — | — |
| Isomalt | Compressible carrier | — | — | 210.04 mg (70% w/w) | — |
| Dextrates | Compressible carrier | — | — | — | 210.04 mg (70% w/w) |
| Sodium Stearyl Fumarate | Lubricant | 3.0 mg (1% w/w) | 3.0 mg (1% w/w) | 3.0 mg (1% w/w) | 3.0 mg (1% w/w) |

TABLE 4

| Ingredient | Function | 14CF20/009 mg/tablet (% w/w) | 14CF20/010 mg/tablet (% w/w) | 14CF20/011 mg/tablet (% w/w) | 14CF20/012 mg/tablet (% w/w) |
| --- | --- | --- | --- | --- | --- |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) |
| Mannitol | Compressible carrier | 105.02 mg (35% w/w) | — | 105.02 mg (35% w/w) | 210.04 mg (70% w/w) |
| Dextrase | Compressible carrier | — | 105.02 mg (35% w/w) | — | — |
| Xylitol | Compressible carrier | 105.02 mg (35% w/w) | 105.02 mg (35% w/w) | 105.02 mg (35% w/w) | — |
| Sodium Stearyl Fumarate | Lubricant | 3.0 mg (1% w/w) | 3.0 mg (1% w/w) | — | — |
| Magnesium stearate | Lubricant | — | — | 3.0 mg (1% w/w) | 3.0 mg (1% w/w) |

Example 5—Weight Stability of Minitab Compositions

Figure 11:
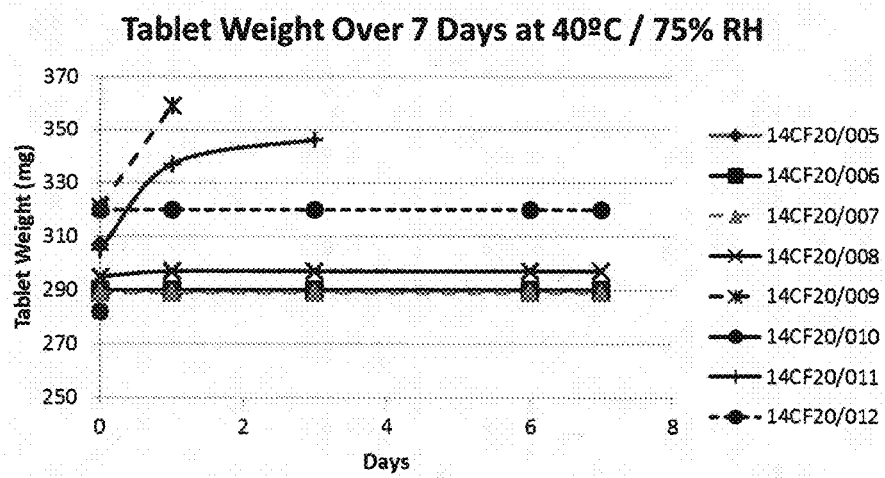
FIG. 11 is a graph showing the change in weight of exemplary tabletted compositions according to the present disclosure when subject to storage for 7 days at 40° C. and 75% relative humidity.

The formulations shown in TABLE 3 and TABLE 4 were weighed at the time for tablet formation. The tablets were stored in open conditions at a temperature of 40° C. and a relative humidity of 75% for 7 days. The tablets were weighed on days 1, 3, 6, 7, and the change in weight was recorded, with any increase in weight being attributed to uptake of ambient water. The results are provided in FIG. 11. Formulations 14CF20/006, 14CF20/007, 14CF20/008, and 14CF20/012 demonstrated no weight gain over a period of 7 days. Formulation 14CF20/011 disintegrated after 3 days. Formulation 14CF20/009 disintegrated after 1 day. Formulations 14CF20/005 and 14CF20/010 disintegrated in less than one day.

Example 6—Chemical Degradation Analysis of Acetaminophen in Minitabs

Formulations 14CF20/006, 14CF20/007, 14CF20/008, and 14CF20/012 were evaluated by high performance liquid chromatography (HPLC) after open storage for 14 days at a temperature of 40° C. and 75% relative humidity. The samples were tested against tablets of identical formulation stored under lab conditions which are typically 20-25° C. and 55-65% relative humidity. The lab stored tablets were controls for the samples that were stored open at the stress storage condition of 40° C./75% RH. In three of the samples, no degradation was observed in that the chromatogram for the openly stored sample was identical to the chromatogram for the lab-stored tablet. In formulation 14CF20/008, an additional peak was observed on the chromatogram indicating the presence of a possible degradation product at an amount of 0.3% relative to the acetaminophen.

Example 7—Chewy Compositions

Exemplary formulations according to the present disclosure for compositions having a chewy texture are shown in TABLE 5 and TABLE 6. Each exemplary chewy composition was prepared to include 80 mg of acetaminophen as the active ingredient using 86.96 mg of ACTIMASK® acetaminophen.

To prepare each formulation, the components (except any lubricant used) were weighed and screened before being placed into a blending vessel (Turbula T2F blender). The active ingredient was added to the blending vessel, and the components were blended for 10 minutes. The sodium stearyl fumarate lubricant was added to the blended components while sifting through a 500 μm sieve, and the mixture was blended for 2 minutes. The final mixture was compressed using a Manesty F single station tablet press to the target tablet weight and hardness.

TABLE 5

| Ingredient | Function | mg/tablet (% w/w) Formulation Number | | | |
|---|---|---|---|---|---|
| | | 14CF21/023 | 14CF21/024 | 14CF21/025 | 14CF21/026 |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) |
| Sodium alginate | Hydrophilic polymer | 60 mg (20% w/w) | 60 mg (20% w/w) | 60 mg (20% w/w) | 60 mg (20% w/w) |
| Pectin | Hydrophilic polymer | 60 mg (20% w/w) | 60 mg (20% w/w) | 60 mg (20% w/w) | 60 mg (20% w/w) |
| Dextrin | Bulking agent | 56.44 mg (19% w/w) | 86.44 mg (29% w/w) | — | — |
| Mannitol | Bulking agent | — | — | 56.44 mg (19% w/w) | — |
| Maltodextrin | Bulking agent | — | — | — | 56.44 mg (19% w/w) |
| Calcium carbonate | Alginate crosslinker | 30 mg (10% w/w) | — | 30 mg (10% w/w) | 30 mg (10% w/w) |
| Citric acid | Acidulant | 3.0 mg (1% w/w) | 3.0 mg (1% w/w) | 3.0 mg (1% w/w) | 3.0 mg (1% w/w) |
| Sucralose | Sweetener | 0.6 mg (0.2% w/w) | 0.6 mg (0.2% w/w) | 0.6 mg (0.2% w/w) | 0.6 mg (0.2% w/w) |
| Sodium stearyl fumarate | Lubricant | 3.0 mg (1% w/w) | 3.0 mg (1% w/w) | 3.0 mg (1% w/w) | 3.0 mg (1% w/w) |

TABLE 6

| Ingredient | Function | mg/tablet (% w/w) Formulation Number | | | | |
|---|---|---|---|---|---|---|
| | | 14CF21/027 | 14CF21/028 | 14CF21/029 | 14CF21/030 | 14CF21/031 |
| Acetaminophen ACTIMASK ® (92%) | Taste-masked API | 86.96 mg (29% w/w) | 86.96 mg (29% w/w) | 86.96 mg (29% w/w) | 86.96 mg (29% w/w) | 86.96 mg (29% w/w) |
| Sodium alginate | Hydrophilic polymer | — | — | — | 30 mg (10% w/w) | 30 mg (10% w/w) |
| Pectin | Hydrophilic polymer | 30 mg (10% w/w) | 30 mg (10% w/w) | 30 mg (10% w/w) | 30 mg (10% w/w) | 30 mg (10% w/w) |
| Acacia | Hydrophilic polymer | 60 mg (20% w/w) | 60 mg (20% w/w) | 60 mg (20% w/w) | 30 mg (10% w/w) | 30 mg (10% w/w) |
| Dextrin | Bulking agent | 116.44 mg (39% w/w) | — | — | — | — |
| Mannitol | Bulking agent | — | — | — | 116.44 mg (39% w/w) | 60 mg (20% w/w) |
| Isomalt | Bulking agent | — | — | 116.44 mg (39% w/w) | — | 56.44 mg (19% w/w) |
| Maltodextrin | Bulking agent | — | 116.44 mg (39% w/w) | — | — | — |
| Citric acid | Acidulant | 3.0 mg (1% w/w) | 3.0 mg (1% w/w) | 3.0 mg (1% w/w) | 3.0 mg (1% w/w) | 3.0 mg (1% w/w) |
| Sucralose | Sweetener | 0.6 mg (0.2% w/w) | 0.6 mg (0.2% w/w) | 0.6 mg (0.2% w/w) | 0.6 mg (0.2% w/w) | 0.6 mg (0.2% w/w) |
| Sodium stearyl fumarate | Lubricant | 3.0 mg (1% w/w) | 3.0 mg (1% w/w) | 3.0 mg (1% w/w) | 3.0 mg (1% w/w) | 3.0 mg (1% w/w) |

Example 8—Weight Stability of Chewy Compositions

Figure 12:
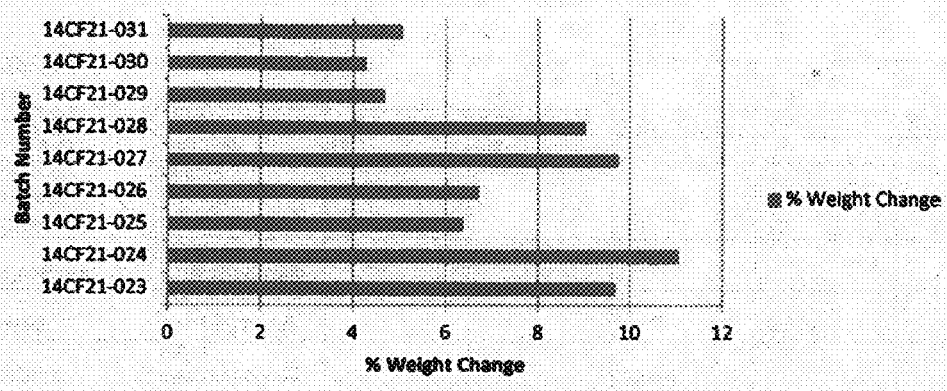
FIG. 12 is a graph showing the change in weight of exemplary chewy compositions according to the present disclosure when subject to storage for 5 days at 40° C. and 75% relative humidity.

The formulations shown in TABLE 5 and TABLE 6 were weighed at the time for tablet formation. The tablets were stored in open conditions at a temperature of 40° C. and a relative humidity of 75% for 5 days, and the change in weight was recorded, with any increase in weight being attributed to uptake of ambient water. The results are provided in FIG. 12.

Example 9—Chemical Degradation Analysis of Acetaminophen in Chewy Compositions

Formulations 14CF21/025, 14CF21/026, 14CF21/029, and 14CF21/030 were evaluated by high performance liquid chromatography (HPLC) after open storage for 11 days at a temperature of 40° C. and 75% relative humidity. The samples were tested against tablets of identical formulation stored under lab conditions which are typically 20-25° C. and 55-65% relative humidity. The lab stored tablets were controls for the samples that were stored open at the stress storage condition of 40° C./75% RH. No degradation was observed in any of the tested samples—i.e., the chromatogram for the openly stored sample was identical to the chromatogram for the lab-stored tablet.

Example 10—Lipid-Based Compositions

Exemplary formulations according to the present disclosure for lipid-based compositions are shown in TABLE 7. Each exemplary lipid-based composition was prepared to include one of the following active ingredients: vitamin C; pantothenic acid; folic acid; acetylsalicylic acid; loratadine; acetaminophen; or ibuprofen.

Each formulation included a combination of white chocolate, milled sugar (sucrose), and corn starch. The white chocolate was a commercially available composition having the following ingredients: 20-30% by weight milk solids; 35-55% by weight sugars; 25-45% by weight total fats; and 0.3-1% by weight legally permitted emulsifiers. Although white chocolate was used, other chocolates (e.g., milk chocolate, dark chocolate, etc.) as also contemplated. To prepare each formulation, the components were weighed and screened before being placed into a blending vessel. The active ingredient was added to the blending vessel, and the components were blended. The final mixture was formed into a unitary structure having a mass of 250 mg.

TABLE 7

| | mg/unit (% w/w) Formulation Number | | | | | | | |
|---|---|---|---|---|---|---|---|---|
| Ingredient | 222121 | 222122 | 222123 | 222124 | 222125 | 222126 | 222127 | 222128 |
| White Chocolate | 85 | 76.8 | 76.7 | 82.0 | 62.1 | 83.6 | 62.3 | 70.9 |
| Milled Sugar | 15 | 13.6 | 13.5 | 14.5 | 11.0 | 14.7 | 11.0 | 12.5 |
| Corn Starch | 5 | 4.5 | 4.5 | 4.8 | 3.6 | 4.9 | 3.6 | 4.2 |
| Vitamin C | — | 9.6 | — | — | — | — | — | — |
| Pantothenic acid | — | — | 9.8 | — | — | — | — | — |
| Folic acid (10% on dextrose | — | — | — | 3.53 | — | — | — | — |
| Acetylsalicylic acid | — | — | — | — | 27.00 | — | — | — |
| Loratadine | — | — | — | — | — | 1.67 | — | — |
| Acetaminophen | — | — | — | — | — | — | 26.67 | — |
| Ibuprofen | — | — | — | — | — | — | — | 16.57 |
| Color/Flavor | q.s | q.s | q.s | q.s | q.s | q.s | q.s | q.s |
| Water | to 100 | to 100 | to 100 | to 100 | to 100 | to 100 | to 100 | to 100 |

Example 11—Gummy Composition

A gummy base suitable for use as an outer composition in an oral, chewable dosage form was prepared using the components shown in TABLE 8. A first solution was formed by combining the gelatin, sucrose, and water at 60° C. A second solution was formed by combining the glucose syrups and sucrose and warming to 60° C. The first and second solutions were combined, and the calcium carbonate was added with mixing. The blended mixture (slurry) was held at 55-60° C. in a batch tank. The slurry was heated to 104° C. and flash cooled to 90° C. to reduce solids to 82/84 Brix. Thereafter, natural flavors and colors were added along with citric acid, and the mixture was placed into molds.

TABLE 8

| Hydrocolloid System Component | Amount (% w/w) |
|---|---|
| Gelatin 250 bloom | 5.89 |
| Pectin CS502 | 0.15 |

TABLE 8-continued

| Hydrocolloid System Component | Amount (% w/w) |
|---|---|
| Sucrose | 2.46 |
| Water (60° C.) | 15.17 |
| Glucose Syrup 63 DE | 28.00 |
| Glucose Syrup 43 DE | 15.00 |
| Sucrose | 25.54 |
| Calcium carbonate | 6.70 |
| Color/Flavor | 1.04 |
| Citric Acid | 0.05 |

Example 12—Gummy Composition

A gummy base suitable for use as an outer composition in an oral, chewable dosage form was prepared using the components shown in TABLE 9. The pectin and carragennan were mixed with the dispersing sucrose and hydrated in the water at 80° C. Separately, the glucoses were heated in the dispersing water to 90° C. The sucrose was added to the glucose/water mixture and heated to 90-100° C. The pectin/carragennan mixture was added to the glucose mixture to form a slurry. The slurry was heated to 104° C. and flash cooled to 90° C. to reduce solids to 82/84 Brix Thereafter, natural flavors and colors were added along with citric acid, and the final composition was deposited into molds.

TABLE 9

| Hydrocolloid System Component | Amount (% w/w) |
|---|---|
| Pectin CS502 | 2.00 |
| Carrageenan 310C | 0.50 |
| Sucrose (to disperse) | 3.00 |
| Water | 20.00 |
| Water (to disperse) | 4.50* |
| Glucose 42 | 16.00 |
| Glucose 63 | 29.00 |
| Sucrose | 24.00 |
| Flavor/Color/Acid | 5.50 |

*Removed during processing

Example 13—Preparation of Oral, Chewable Dosage Form

An oral, chewable dosage form was prepared by forming a core composition as described herein and forming a gummy base as described herein. A portion of the gummy base composition was deposited into a mold to form a base (or cap) of the dosage form. The core was placed on top of the deposited gummy base portion. The remaining gummy base mixture was added to the mold to cover and fully surround the core. The dosage form was then cooled to a defined profile to allow for a controlled setting rate.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A chewable, multicomponent composition for oral administration, the multicomponent composition comprising:
   a first component that is a hydrocolloid system comprising about 70% to about 94% w/w of one or more hydrophilic bulking agents, about 1% to about 20% w/w of one or more hydrophilic, long-chain polymers, and about 5% to about 35% w/w of a water source, the first component being in the form of a gel;
   a second component that is a solid unit or plurality of solid units in the form of a pre-formed tablet having a hardness of about 2 Kp to about 20 Kp; and
   an active ingredient;
   wherein the first component comprises at least a portion of an outer surface of the multicomponent composition.

2. The multicomponent composition of claim 1, wherein the first component completely surrounds the second component such that the first component is a shell surrounding at least one core formed of the second component.

3. The multicomponent composition of claim 2, further comprising a third component configured as a layer between the first component and the second component.

4. The multicomponent composition of claim 3, wherein the third component is configured as a barrier layer that substantially prevents passage of water between the first component and the second component.

5. The multicomponent composition of claim 1, wherein one or more of the following conditions is met:
   the active ingredient is included in the second component;
   the active ingredient is included in the first component;
   the active ingredient is in an encapsulated form;
   the gummy composition is elastic or viscoelastic;
   the multicomponent composition further comprises an outer layer surrounding the first component and the second component.

6. The multicomponent composition of claim 1, wherein the active ingredient is a natural or synthetic substance that is recognized as being beneficial to human health and is selected from the group consisting of non-steroidal anti-inflammatory drugs (NSAIDs), analgesics, antihistamines, decongestants, antitussives, expectorants, sleep aids, antibiotics, laxatives, anti-diarrheals, anthelmintics, antacids, vitamins, minerals, phytonutrients, fiber, fatty acids, amino acids, polypeptides, botanicals, herbs, prebiotics, probiotics, and combinations thereof.

7. The multicomponent composition of claim 1, wherein one or more of the following conditions is met:
   the one or more hydrophilic bulking agents includes one or more saccharides or saccharide derivatives;
   the one or more hydrophilic bulking agents includes one or more hydrogenated carbohydrates;
   the one or more hydrophilic bulking agents includes one or both of sugar solids and granulated sugar;
   the one or more hydrophilic bulking agents includes glucose, sucrose, and sorbitol.

8. The multicomponent composition of claim 1, wherein the second composition comprises one or more ingredients selected from the group consisting of saccharides, saccharide derivatives, lipids, cellulosic polymers, cellulosic polymer derivatives, inorganic salts, and combinations thereof.

9. The multicomponent composition of claim 1, wherein the second composition is a pre-formed solid unit in the form of one or more of a tablet, a caplet, a hard shell capsule, a soft shell capsule, a microcapsule, and a pastille.

10. The multicomponent composition of claim 1, wherein the pre-formed tablet comprises about 5% to about 80% w/w of one or more bulking agents, about 0.1% to about 15% w/w of one or more disintegrants, about 0.05% to about 5% w/w of one or more processing aids, and the active ingredient in an amount of about 0.1% to about 60% w/w.

11. The multicomponent composition of claim 1, wherein one or both of the following conditions is met:
   the pre-formed tablet is stable such that the active ingredient exhibits substantially no degradation when the core composition is stored for a time of 20 days at a temperature of 40° C. and a relative humidity of 75%;
   the pre-formed tablet is stable such that, separate from the first component, the pre-formed tablet absorbs less than about 5% by weight of water (based on the weight of the tabletted composition) over a time of 14 days at a temperature of 40° C. and a relative humidity of 75%.

12. The multicomponent composition of claim 1, wherein the pre-formed tablet has a diameter of about 6 mm to about 12 mm and a thickness of about 0.5 mm to 8 mm; or wherein the pre-formed tablet has a diameter of about 2 mm to about 10 mm and a thickness of about 0.5 mm to 6 mm.

13. The multicomponent composition of claim 1, wherein the second composition is a pre-formed unit of a lipidic composition that comprises one or more lipidic materials and one or more bulking agents.

14. The multicomponent composition of claim 13, wherein the one or more lipidic materials are selected from the group consisting of vegetable fats, nut fats, seed fats, and combinations thereof.

15. The multicomponent composition of claim 13, wherein the one or more lipidic materials comprises cocoa fat.

16. The multicomponent composition of claim 13, wherein the pre-formed unit of the lipidic composition comprises about 10% to about 60% w/w of the one or more lipid materials and about 10% to about 60% w/w of the one or more bulking agents.

17. The multicomponent composition of claim 13, wherein the active ingredient is present in the pre-formed unit of the lipidic composition, and wherein the pre-formed unit of the lipidic composition is stable such that, after being stored for a time of 28 days at a temperature of 50° C. and a relative humidity of 60%, the pre-formed unit of the lipidic composition comprises less than about 2% by weight of active ingredient degradation products relative to the weight of the active ingredient.

18. The multicomponent composition of claim 13, wherein the pre-formed unit of the lipidic composition has a diameter of about 0.5 mm to about 10 mm.

19. The multicomponent composition of claim 1, wherein the second composition is in the form of a particulate material.

20. The multicomponent composition of claim 19, wherein the particulate material is in the form of a powder, granules, beads, or combinations thereof.

21. The multicomponent composition of claim 1, wherein the first component is hydrocolloid system comprising about 70% to about 94% w/w of one or more saccharides or saccharide derivatives, about 1% to about 15% w/w of one or more hydrophilic, long-chain polymers comprising at least pectin, and about 10% to about 25% w/w of a water source, the first component being in the form of a gel.

22. The multicomponent composition of claim 1, wherein the first component is one or both of configured to be reduced to smaller pieces through mastication and configured to dissolve within the mouth.

* * * * *